(12) United States Patent
Wasielewski

(10) Patent No.: US 8,814,877 B2
(45) Date of Patent: Aug. 26, 2014

(54) USE OF MICRO- AND MINIATURE POSITION SENSING DEVICES FOR USE IN TKA AND THA

(75) Inventor: Ray C. Wasielewski, New Albany, OH (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/546,641

(22) Filed: Jul. 11, 2012

(65) Prior Publication Data

US 2012/0277752 A1 Nov. 1, 2012

Related U.S. Application Data

(62) Division of application No. 12/342,795, filed on Dec. 23, 2008, now Pat. No. 8,241,296, which is a division of application No. 10/820,279, filed on Apr. 8, 2004, now abandoned.

(60) Provisional application No. 60/461,173, filed on Apr. 8, 2003.

(51) Int. Cl.
*A61B 17/56* (2006.01)
(52) U.S. Cl.
USPC .......................................................... 606/91

(58) Field of Classification Search
USPC ..................... 606/53, 86 R, 87, 96, 102, 130; 623/16.11, 22.11, 22.12, 23.16, 914; 600/301, 424, 587, 594, 595; 128/903
See application file for complete search history.

(56) References Cited

U.S. PATENT DOCUMENTS 6,447,448 B1 * 9/2002 Ishikawa et al. .............. 600/300

* cited by examiner

*Primary Examiner* — Pedro Philogene
*Assistant Examiner* — David Comstock
(74) *Attorney, Agent, or Firm* — Norton Rose Fulbright Canada LLP

(57) ABSTRACT

A system for assisting in a surgical process, comprising: (a) a surgical device taken from a group consisting of a surgical tool and a surgical implant; (b) a positional sensor carried by the surgical device, the positional sensor including a wireless transmitter and associated circuitry for transmitting sensor data from the transmitter; and (c) a computer system including a wireless receiver and signal conditioning circuitry and hardware for converting sensor data received by the wireless receiver into at least one of (i) audio feedback of positional information for the surgical device and (ii) visual feedback of positional information for the surgical device.

19 Claims, 19 Drawing Sheets

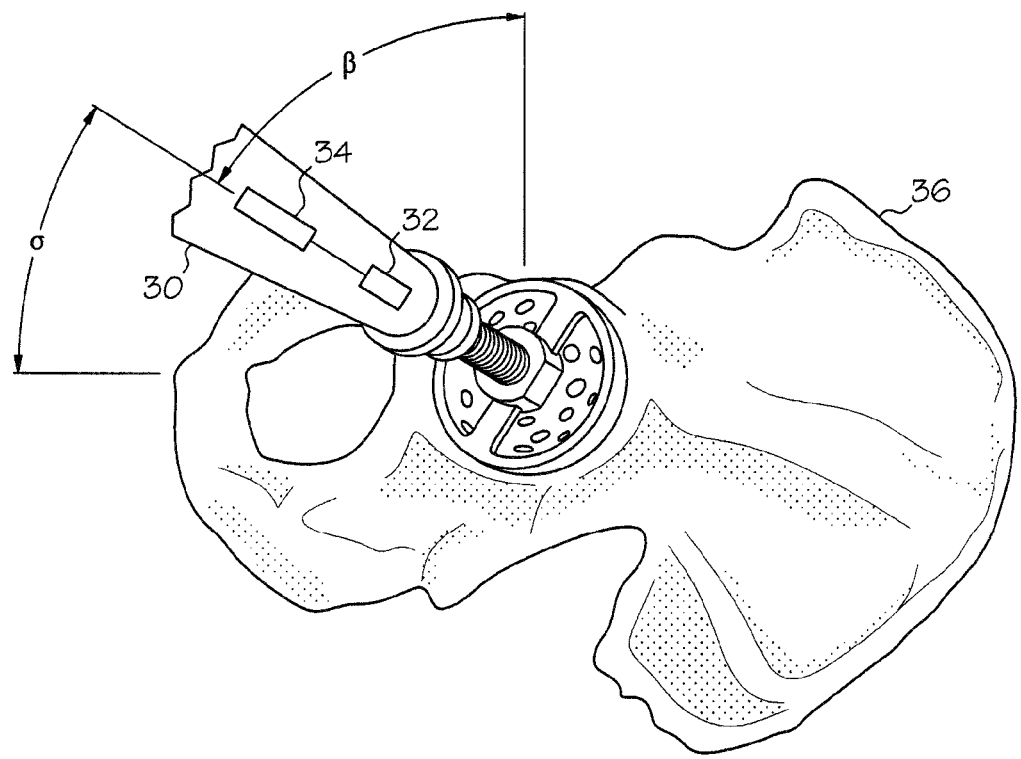
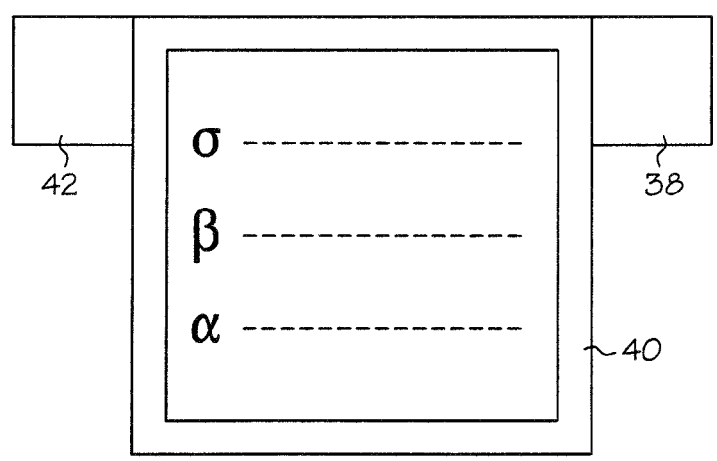
FIG. 2

USE OF MICRO- AND MINIATURE POSITION SENSING DEVICES FOR USE IN TKA AND THA

CROSS REFERENCE TO RELATED APPLICATIONS

This is a Divisional Application of U.S. patent application Ser. No. 12/342,795 filed Dec. 23, 2008 now U.S. Pat. No. 8,241,296, which is a Divisional Application of U.S. patent application Ser. No. 10/820,279 filed Apr. 8, 2004 now abandoned, which claims the benefit of priority of U.S. Provisional Patent Application Ser. No. 60/461,173 entitled "USE OF MICRO- AND MINIATURE POSITION SENSING DEVICES FOR USE IN TKA AND THA" filed Apr. 8, 2003, the disclosure of which are expressly incorporated by reference herein in their entirety.

BACKGROUND

Image guided surgery is being evaluated to assist a surgeon in positioning various implant components in joint arthroplasty. These image-guided systems typically rely on infrared sensors to gauge the position of the prosthetic devices and jigs in the three coordinate system. However, these systems are bulky and may also require one or more of the components thereof to be mounted to bone. In addition, these systems require a direct line of sight that makes it difficult for the surgeon to both operate and "stay out of the way" of the infrared transmissions. It is highly unlikely that these bulky devices will be useful in the small confines of minimally invasive surgery where direct line of sight will be at a premium. Additionally, the time required to use these devices can extend surgery time substantially.

SUMMARY

The present invention is directed to miniature sensing devices for use in surgical procedures and devices used therein. The invention utilizes, at least in part, generally two classes of devices: micro- and miniature sensing devices and associated micro- and miniature transmitting devices. Data from the sensing devices may be transmitted by the transmitting devices wirelessly to one or more data conditioning devices that may be operatively coupled to or include one or more displays and/or data recording devices. In an exemplary embodiment, the sensors include microgyroscopes oriented to output data relevant to three axes of position and/or movement. The microgyroscopes are operatively coupled to a wireless transmitter for transmitting the positional data to a data conditioning device, which may be operatively coupled to or include a visual display and a data recording device. Exemplary transmission protocols include, without limitation, ISM (b) and FSK modulation or spread spectrum modulation.

In a further detailed exemplary embodiment, the micro- or miniature sensors of the present invention may be mounted to surgical tools such as individual cutting jigs, alignment instrumentation (e.g., acetabular reamers, extramedullary tibial cutter), prosthetic trials and positioning devices (e.g., cup inserter), final prosthetic devices (e.g., central screw in acetabular shell), and/or the patient (e.g., to the patient's bone or other tissue). The micro- or miniature sensing devices generate data, such as position data in the three coordinates, orientation data, and/or movement data, that is transmitted to a data conditioning device. Exemplary data conditioning devices may be operatively coupled to or include, without limitation, visual displays for simulating virtual surgical environments, auditory advisory devices, and/or a computer to track the movement of the surgical device during the surgical procedure. The differing size restrictions for various surgical procedures and surgical equipment may be significant factors in the choice of sensing devices and transmission methodology. In addition to the micro- or miniature gyroscopes, additional sensing devices adapted for use with the present invention may include, without limitation, micro- or miniature inclinometers, accelerometers, and magnetometers.

The present invention is discussed in exemplary form with respect to joint arthroplasty, however, the exemplary embodiments disclosed herein may be applicable to further surgical procedures and equipment apparent to one of ordinary skill and likewise fall within the scope of the present invention.

Therefore it is a first aspect of the present invention to provide a system for assisting in a surgical process, comprising: (a) a surgical device taken from a group consisting of a surgical tool and a surgical implant; (b) a positional sensor carried by the surgical device, the positional sensor including a wireless transmitter and associated circuitry for transmitting sensor data from the transmitter; and (c) a computer system including a wireless receiver and signal conditioning circuitry and hardware for converting sensor data received by the wireless receiver into at least one of (i) audio feedback of positional information for the surgical device and (ii) visual feedback of positional information for the surgical device.

It is a second aspect of the present invention to provide a system for assisting in a surgical process, comprising: (a) a surgical device taken from a group consisting of a surgical tool, a prosthetic component, and a surgical implant; (b) a sensor carried by the surgical device, the sensor operatively coupled to a wireless transmitter and associated circuitry for transmitting sensor data including at least one of positional data and orientational data outputted from the sensor; and (c) a computer system including a visual display, a wireless receiver, and signal conditioning circuitry and hardware for converting the sensor data received by the wireless receiver into visual feedback information for viewing on the visual display.

It is a third aspect of the present invention to provide a surgical telemetry system comprising: (a) a sensor mounted to a surgical device, the sensor taken from the group consisting of an accelerometer, a magnetometer, a gyroscope, or an inclinometer; (b) a digital processing device operatively coupled to the sensor to receive data derived from data output from the sensor, the digital processing device generating a display output; and (c) a display operatively coupled to the digital processing device and adapted to receive the display output, where the display output displays the change in at least one of position and orientation of the sensor with respect to a point of reference.

It is a fourth aspect of the present invention to provide a surgical telemetry system comprising: (a) a computer system having signal conditioning hardware and software; (b) a surgical instrument having an instrument positional sensor carried thereon, the instrument positional sensor being operatively coupled to the signal conditioning hardware and software of the computer system to transmit instrument positional data thereto; and (c) a prosthetic component having a prosthetic component positional sensor carried thereon, the prosthetic component positional sensor being operatively coupled to the signal conditioning hardware and software of the computer system to transmit prosthetic component positional data thereto.

It is a fifth aspect of the present invention to provide a surgical telemetry system comprising: (a) a computer system having signal conditioning hardware and software; (b) a first surgical instrument having a first instrument positional sensor carried thereon, the first instrument positional sensor being operatively coupled to the signal conditioning hardware and software of the computer system to transmit first instrument positional data thereto; and (c) a second surgical instrument having a second instrument positional sensor carried thereon, the second instrument positional sensor being operatively coupled to the signal conditioning hardware and software of the computer system to transmit second instrument positional data thereto.

It is a sixth aspect of the present invention to provide a surgical telemetry system comprising: (a) a computer system having signal conditioning hardware and software; (b) a field generating device generating a detectable field approximate a reference object; and (c) at least one of a surgical instrument and a prosthetic component having a sensor carried thereon for sensing the detectable field, the sensor being operatively coupled to the signal conditioning hardware and software of the computer system to transmit positional data thereto relative to the detectable field.

It is a seventh aspect of the present invention to provide a surgical telemetry system comprising: (a) a sensor mounted to a prosthetic trial, the sensor including at least one of an accelerometer, a magnetometer, a gyroscope, and an inclinometer; and (b) a wireless transmitter operatively coupled to the sensor to disseminate broadcast data derived from output data attributable to the sensor.

It is an eighth aspect of the present invention to provide a surgical telemetry system comprising: (a) a sensor mounted to a prosthetic component, the sensor including at least one of an accelerometer, a magnetometer, a gyroscope, and an inclinometer; and (b) a wireless transmitter operatively coupled to the sensor to disseminate broadcast data derived from output data attributable to the sensor.

It is a ninth aspect of the present invention to provide a surgical telemetry system comprising: (a) a sensor mounted to a surgical jig, the sensor including at least one of an accelerometer, a magnetometer, a gyroscope, and an inclinometer; and (b) a wireless transmitter operatively coupled to the sensor to disseminate broadcast data derived from output data attributable to the sensor.

It is a tenth aspect of the present invention to provide a surgical telemetry system comprising: (a) a sensor mounted to a surgical device, the sensor including at least one of an accelerometer, a magnetometer, a gyroscope, and an inclinometer; and (b) a wireless transmitter operatively coupled to the sensor to disseminate broadcast data derived from output data attributable to the sensor, where the surgical device is utilized in at least one of a total knee arthroplasty procedure and a total hip arthroplasty procedure.

It is an eleventh aspect of the present invention to provide a surgical telemetry system comprising: (a) a sensor mounted to a surgical implant, the sensor including at least one of an accelerometer, a magnetometer, a gyroscope, or an inclinometer; (b) a digital processing device operatively coupled to the sensor to receive data derived from data output from the sensor, the digital processing device generating a display output; and (c) a display operatively coupled to the digital processing device and adapted to receive the display output, where the display output displays the change in at least one of position and orientation of the sensor with respect to a point of reference.

It is a twelfth aspect of the present invention to provide a surgical telemetry system comprising: (a) a surgical instrument having an instrument positional sensor associated therewith, the instrument positional sensor coupled to a wireless transmitter to transmit output data from the instrument positional sensor indicative of the position of the surgical instrument; (b) an implantable prosthetic device having a prosthetic device positional sensor associated therewith, the prosthetic device positional sensor coupled to a wireless transmitter to transmit output data from the prosthetic device positional sensor indicative of the position of the implantable prosthetic device; (c) a surgical jig having a jig positional sensor associated therewith, the jig positional sensor coupled to a wireless transmitter to transmit output data from the jig positional sensor indicative of the position of the surgical jig; (d) an anatomical positional sensor adapted to be mounted to an anatomical feature of a patient, the anatomical positional sensor coupled to a wireless transmitter to transmit output data from the anatomical positional sensor indicative of the position of the anatomical feature; and (e) a data processing device comprising: (i) a receiver adapted to receive the transmitted output data, (ii) processing circuitry to transform the transmitted output data, (iii) a digital device operatively coupled to the processing circuitry including software operative to convert transformed sensor output data into relative position data adapted to be viewable to reflect at least one of position and orientation of at least one of the surgical instrument, the implantable prosthetic device, the surgical jig, and the anatomical positional sensor, and (iv) a visual display for viewing the relative position data.

It is a thirteenth aspect of the present invention to provide a method of supplementing a surgical procedure using a surgical telemetry system comprising: (a) using a surgical device including a sensor mounted thereto, the sensor taken from the group consisting of an accelerometer, a magnetometer, a gyroscope, or an inclinometer, and the surgical device taken from the group consisting of a surgical instrument, a prosthesis or a surgical jig; (b) operatively coupling the sensor of the surgical device to at least one of a wired receiver and a wireless receiver to receive output data generated by the sensor indicative of at least one of position data and orientation data; and (c) generating feedback data derived from the output data of the sensor.

It is a fourteenth aspect of the present invention to provide a method of manufacturing a medical device, the method comprising the steps of: (a) associating at least one of an accelerometer, a gyroscope, a magnetometer, and an inclinometer with a medical device; and (b) associating a wireless transmitter with at least one of an accelerometer, a gyroscope, a magnetometer, and an inclinometer, where the wireless transmitter is adapted to transmit wireless data derived from output data from at least one of the accelerometer, the gyroscope, the magnetometer, and the inclinometer.

It is a fifteenth aspect of the present invention to provide a method of manufacturing a prosthetic device, the method comprising the steps of: (a) associating at least one of an accelerometer, a gyroscope, a magnetometer, and an inclinometer with a prosthetic device; and (b) associating a wireless transmitter with at least one of an accelerometer, a gyroscope, a magnetometer, and an inclinometer, where the wireless transmitter is adapted to transmit wireless data derived from output data from at least one of the accelerometer, the gyroscope, the magnetometer, and the inclinometer.

It is a sixteenth aspect of the present invention to provide a method of generating telemetry data regarding the position of an object during a surgical procedure, the method comprising the steps of: (a) receiving a transmission from a transmitter operatively coupled to at least one of an accelerometer, a gyroscope, a magnetometer, and an inclinometer associated with at least one of a medical device and a prosthetic device adapted for use with a surgical procedure; (b) processing the transmission from the transmitter into a format amendable to visual display; and (c) displaying the format onto the visual display such that changes in position of at least one of the medical device and the prosthetic device are reflected in substantially real-time and correspond substantially to an actual position of at least one of the medical device and the prosthetic device.

It is a seventeenth aspect of the present invention to provide a method of manufacturing a surgical device, the method comprising the steps of: (a) associating at least one of an accelerometer, a gyroscope, a magnetometer, and an inclinometer with a surgical device; and (b) associating a wireless transmitter with at least one of the accelerometer, the gyroscope, the magnetometer, and the inclinometer, where the wireless transmitter is adapted to transmit wireless data derived from output data from at least one of the accelerometer, the gyroscope, the magnetometer, and the inclinometer.

It is an eighteenth aspect of the present invention to provide a method of generating telemetry data regarding the position of an object during a surgical procedure, the method comprising the steps of: (a) receiving a transmission from a transmitter operatively coupled to at least one of an accelerometer, a gyroscope, a magnetometer, and an inclinometer associated with at least one of a surgical device, an implant, and a prosthetic component adapted for use with a surgical procedure; (b) processing the transmission from the transmitter into a format amendable to visual display; and (c) displaying the format onto a visual display such that changes in position of at least one of the medical device and the prosthetic device are reflected in substantially real-time and correspond substantially to an actual position of at least one of the medical device and the prosthetic device.

BRIEF DESCRIPTION OF THE DRAWINGS

FIG. 2 is a representative and schematic view of an exemplary embodiment of the present invention;

DESCRIPTION OF THE PRESENT INVENTION

The present invention is directed to systems and associated methods that may provide visual or other telemetry regarding the orientation and/or position of surgical devices and jigs, anatomical features, and/or final and trial prosthetic components for use with surgical procedures such as, without limitation, total hip arthroplasty and total knee arthroplasty.

As discussed herein, the present invention may be incorporated with various medical devices such as, without limitation, saws, drills, hammers, reamers, screwdrivers, cup alignment instruments, guide-rods of an intramedullary femoral and tibial cutting jig, and extramedullary femoral and tibial cutting jigs. The invention may also be incorporated with various final and trial prosthetic components such as, without limitation, cup inserters, screw cap domes, prosthetic knee tibial trays, prosthetic knee trial stems, prosthetic knee trial tibial trays, prosthetic knee femoral components, prosthetic knee trial femoral components, and intramedullary extensions and stems. Still further, the invention may also be incorporated with implanted devices not encompassed by prosthetics or prosthetic trails.

Figure 1:
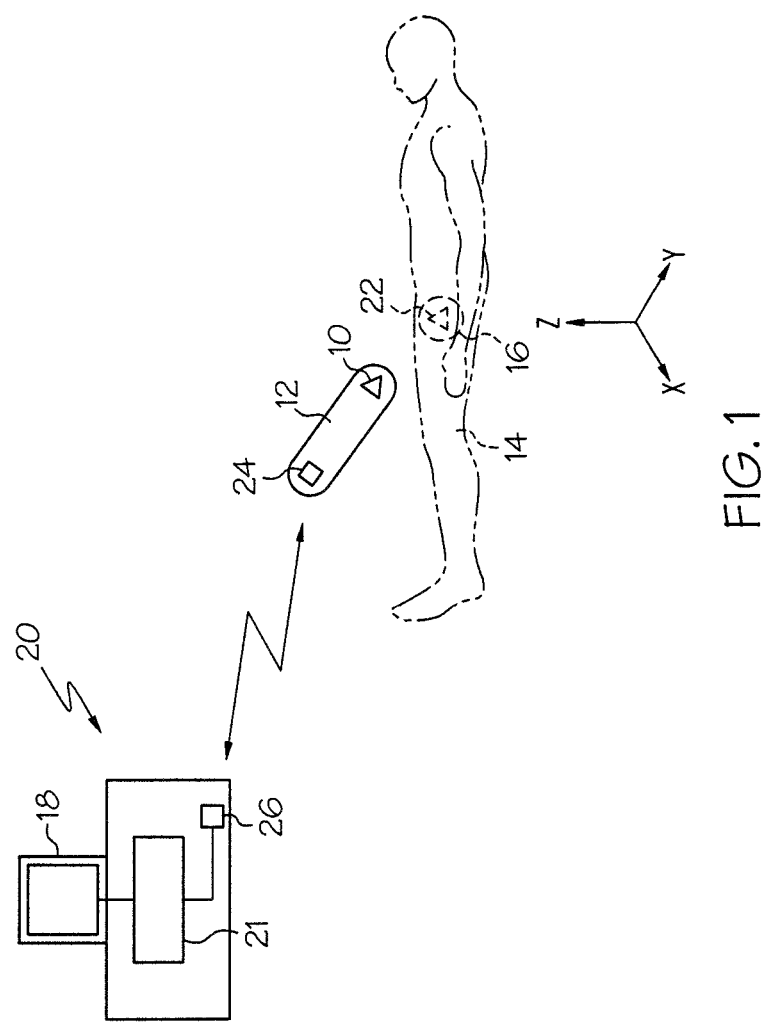
FIG. 1 is a schematic representation of the system according to an exemplary embodiment of the present invention.

Referring to FIG. 1, the invention utilizes one or more micro- or miniature sensors 10 mounted to or within (carried by) a surgical device 12, an anatomical feature of a patient 14, and/or a final or trial prosthetic component 16 to generate feedback or telemetry data during a surgical procedure regarding the position and/or orientation of the device, anatomical feature, and/or the component alone, with respect to one another, and/or with respect to a reference point. As discussed in more detail below, each micro- or miniature sensor 10 outputs data regarding position, orientation and/or movement of that sensor which is indicative of the position and/or orientation of the device, anatomical feature, or component which carries it. In specific embodiments, such output data is generated in real-time and continues to be generated in a three dimensional coordinate system as the sensor changes position and/or orientation.

The sensor output data may be utilized to generate a visual representation of the position and/or orientation of the device, anatomical feature, or component using a visual display 18. A display system 20 may include signal conditioning hardware and software 21 for receiving sensor data from the sensor and for converting such sensor data into a visual image on a visual display 18 operatively coupled thereto or included therewith. Exemplary visual displays may include, for example and without limitation, a television screen, a computer monitor, a projected image, and a virtual reality headset/visor. In this manner, a surgeon (or any other party) can visually discern substantially in real-time the position and/or orientation of the device, feature, or component and any changes thereto during a surgical procedure within the operating room or even from a remote location. This may be particularly useful during surgical procedures where a direct line of sight from a particular angle may not be possible, for instance, in minimally invasive surgery characterized by small incisional openings.

The conditioning hardware and software 21 of the display system 20 may have access to three dimensional maps of the surgical devices and prosthetic components, including data indicative of the location of the micro- or miniature sensors carried thereby, to facilitate the generation of an electronic 3-D image of the devices and prosthetic components. With these 3-D maps in place, the sensor output data may be associated with the 3-D images to create correlated 3-D data in a one-to-one manner showing any actual change in position of the device or component. It is likewise within the scope of the invention that the image data is not generated in a one-to-one manner such that the device or component may be visually magnified for viewing ease and effect. Generally, an increase in the number of strategically positioned sensors carried by a particular surgical device will result in a more accurate the 3-D correlation.

Many applications of the present invention will involve providing additional micro- or miniature reference sensors 22 on one or more reference objects so that the conditioning hardware and software 21 of the display system 20 will be configured to generate displays representing the position, orientation and/or movement of the surgical devices with respect to the reference object(s). Exemplary reference objects may include a patient's bone or other point on the patient's anatomy, an implant, a prosthetic trial component, a final prosthetic component, another surgical tool or instrument, a device worn by the patient, and an operating room object such as an operating table or restraining device. Such reference sensors will also output data regarding position, orientation and/or movement indicative of the position and/or orientation of the device, anatomical feature, or component which carries it. In specific embodiments, such output data is generated in real-time and continues to be generated in a three dimensional coordinate system as the reference sensor changes position and/or orientation. The reference sensor output data may be utilized to generate a visual representation of the position and/or orientation of the reference device, anatomical feature, or component using the visual display 18. In specific embodiments, the conditioning hardware and software 21 of the display system 20 may have access to three dimensional maps of the reference objects, including data indicative of the location of the reference micro- or miniature sensors 22 carried thereby, to facilitate the generation of an electronic 3-D image of the reference objects.

An exemplary use of the present invention includes "targeting". Targeting includes identifying the relative location and/or orientation of one or more surgical devices, prosthetic components, implants, anatomical features, and surgical jigs. An exemplary instance may include a prosthetic trial femoral component being coupled to a surgical stem inserter by way of a threaded interface between the stem of the inserter and the proximal shoulder of the trial femoral component for use in a total hip arthroplasty procedure. After the trial femoral component is positioned within the femur, the inserter may be rotated to disengage from the femoral component so that the surgeon may test the range of motion of the patient's hip without having the inserter as an obstruction. Targeting includes utilizing sensors or other articles associated with the trial component to ascertain the position and/or orientation of the trial component, as well as sensors or other articles associated with the inserter to ascertain the position and/or orientation of the inserter. Thus, the surgeon can align the inserter with the opening within the shoulder of the trial femoral component and engage the inserter with the trial femoral component to facilitate removal of the trial femoral component without with a direct line of sight, such as, without limitation, in minimally invasive surgery. It is to be understood that targeting simply refers to knowing the position and/or orientation of at least one of a surgical device, a prosthetic component, an implant, an anatomical feature, and a surgical jig with respect to a point of reference, and optionally being able to engage or disengage a device without a direct line of sight.

Further exemplary uses of the present invention include monitoring the progress of a surgical instrument, such as the current depth of a reaming instrument, toward the intended goal position, which may or may not be or include a reference object. An exemplary monitoring function might also include providing orientation and position feedback such as how far apart a device or tool is from a prosthetic component or whether or not the surgeon is correctly orienting the surgical instrument, the prosthetic component, or the surgical jig with respect to an intended target position and/or orientation.

The surgical devices, prosthetic components, implants, and surgical jigs include one or more micro- or miniature sensors 10 that output data regarding the position, orientation, and/or movement of structures mounted thereto or incorporated therewith. In an exemplary form, the micro- or miniature sensors may include three or more microgyroscopes carried by the device, component, implant, or jig 12 that are positioned/oriented such that each microgyroscope outputs data regarding changes in one of the X, Y, and Z planes in a three dimensional coordinate system. The microgyroscopes are operatively coupled to one or more micro- or miniature RF transmitters 24 that are also carried by the device, component, implant, or jig 12, where the RF transmitter transmits sensor output data from the microgyroscopes to an RF receiver 26 provided by the display system 20. As discussed above, the surgical devices, prosthetic components, and surgical jigs may be 3-D mapped to assist the conditioning hardware and software 21 of the display system 20 in generating an electronic, virtual representation of the surgical device, prosthetic component, implant, or surgical jig on the associated display. Sensor output data is utilized by the conditioning hardware and software 21 of the display system 20 to impart substantially real-time position, orientation, and/or movement to the virtual representation shown on the display screen 18.

Referencing FIG. 2, a first detailed exemplary application of the present invention includes a surgical reamer 30 adapted for use with a total hip arthroplasty procedure and having at least one micro- or miniature sensor 32 associated therewith. An exemplary sensor 32 may include individually or in combination, without limitation, inclinometers, accelerometers, magnetometers, and microgyroscopes. The sensor 32 is coupled to a micro- or miniature transmitter device 34, which may be carried on the surgical reamer 30, to wirelessly broadcast sensor data regarding the position and/or orientation of the surgical reamer 30 with respect to the pelvis 36 in three axes of movement, represented by planes .beta., .alpha. and .theta. A wireless receiver 38, operatively coupled to a display system 40, receives the signals broadcast by the transmitter 34 and forwards the data derived from the signals for display upon the system 40. The display system 40 is designed to inform the surgeon regarding the position and/or orientation of the surgical reamer 30, for example, continuously during surgery. In a further exemplary embodiment, the surgical reamer 30 may include one or more micro- or miniature sensors strategically carried thereon capable of sensing changes in position, orientation, and/or movement in one or more of the axes of movement.

In a more detailed exemplary embodiment, films of a patient to undergo total hip arthroplasty are taken preoperatively and are utilized to create registration and calculate the depth of acetabular reaming necessary during the procedure. Thereafter, such calculations are input into a data positioning device 42, operatively coupled to the display 40, to reflect the position of the reamer 30 with respect to the patient's pelvis 36. Alternatively, the data positioning device 42 may be operatively coupled to the reamer 30 to interface with the sensor 32 and measure conditions indicative of the orientation and/or position of the reamer 30 relative to the current depth of the reaming and/or the predetermined depth necessary for proper reaming. In accordance with the predetermined calculations, where such measurements may be independent of bone position, the reamer 30 may be automatically stopped or slowed if the desired position and/or orientation of the reamer is outside of a predetermined tolerance. By way of example, and not a limitation, the reamer 30 may be slowed or turned off if the orientation and/or position data reflects that too deep of a depression is being created by the surgeon reaming the acetabulum of the pelvis 36. Likewise, if the reaming appears to be awry from the intended orientation, the reamer will slow or stop to discontinue reaming in the awry orientation.

Figure 3:
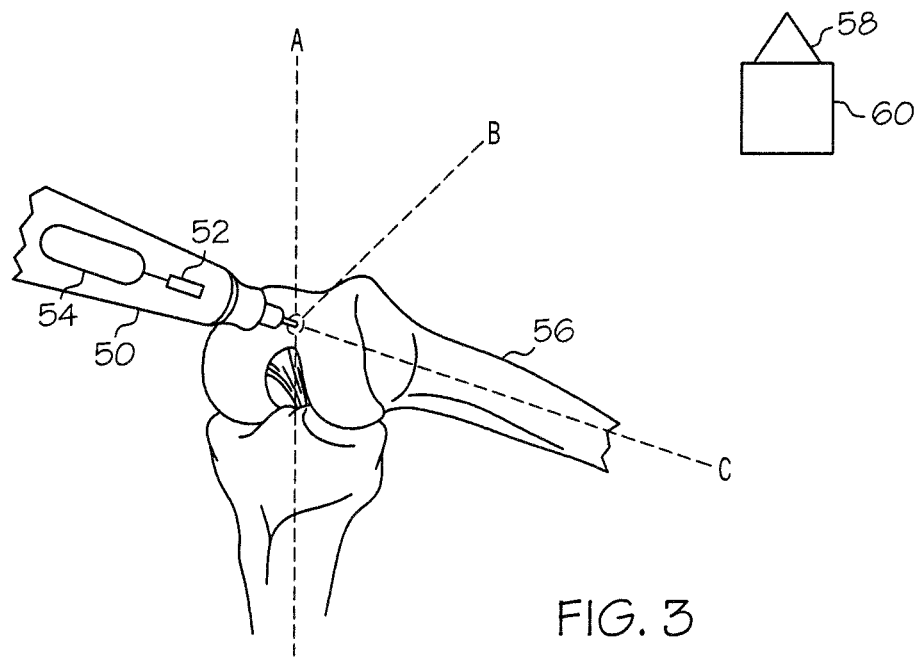
FIG. 3 is a representative and schematic view of an exemplary embodiment of the present invention.
Figure 4:
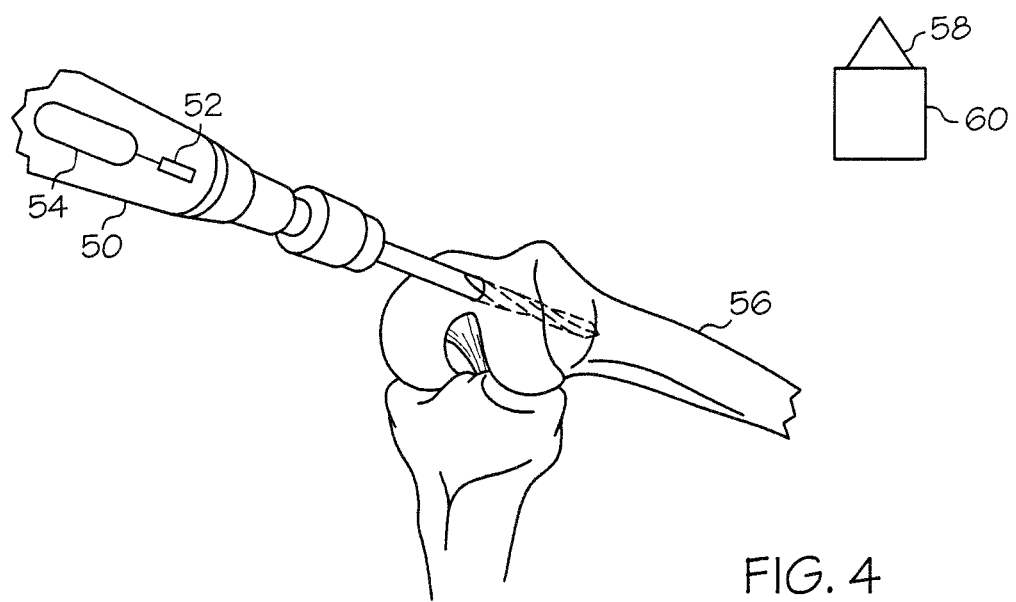
FIG. 4 is a representative and schematic view of an exemplary embodiment of the present invention.

Referring to FIGS. 3 and 4, a second detailed exemplary application may include one or more micro- or miniature sensors 52 associated with a surgical drill 50 and an intramedullary hole starter 50' that may be used in a total knee arthroplasty procedure to facilitate correct positioning of the intramedullary stems and placement of the intramedullary locator. Exemplary sensors 52 may include individually or in combination, without limitation, inclinometers, accelerometers, magnetometers, and microgyroscopes. The sensor 52 may be coupled to a micro- or miniature transmitter device 54, which may also be carried on the surgical drill 50 or the intramedullary hole starter 50', to wirelessly broadcast sensor data regarding the position and/or orientation of the surgical drill and bit 50 or the intramedullary hole starter 50' with respect to a patient's femur 56 in three axes of movement, represented by planes A, B, and C. A wireless receiver 58, operatively coupled to a display system 60, receives the signals broadcast by the transmitter 54 and forwards the data derived from the signals for display upon the system 60. The display system 60 is designed to inform the surgeon regarding the position and/or orientation of the surgical drill 50 or the intramedullary hole starter 50' to ensure proper alignment with respect to the femur 56. In a further exemplary embodiment, the surgical drill 50 and/or the intramedullary hole starter 50' may include at least three micro- or miniature sensors strategically carried thereon capable of sensing changes in position, orientation, and/or movement in three axes. In yet another exemplary embodiment, the surgical drill 50 and/or the intramedullary hole starter 50' may include fewer than three sensors providing position and/or orientation data in less than three axes of movement.

Figure 5:
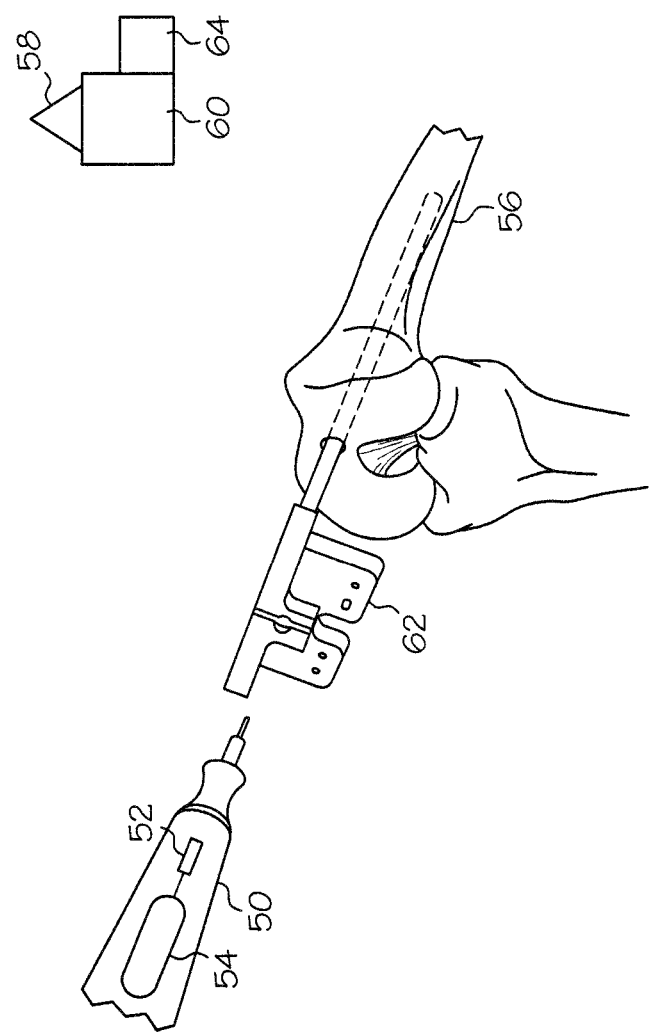
FIG. 5 is a representative and schematic view of an exemplary embodiment of the present invention.

Referencing FIGS. 4 and 5, in a more detailed exemplary embodiment, films of a patient to undergo total knee arthroplasty are taken preoperatively and are utilized to calculate the depth of drilling necessary for proper accommodation of one or more surgical jigs 62 and component stems. Thereafter, such calculations are input into a data positioning device 64, operatively coupled to the display 60 to reflect the position of the drill 50 with respect to the patient's femur 56. Alternatively, the data positioning device 64 may be operatively coupled to the drill 50 to interface with the sensor 52 and measure conditions indicative of the orientation and/or position of the drill 50 relative to a predetermined depth. In accordance with the predetermined calculations, the drill 50 may be automatically stopped or slowed if the desired position and/or orientation of the drill bit is outside of a predetermined tolerance. By way of example, and not a limitation, the drill 50 may be slowed or turned off if the orientation and/or position data reflects that the alignment of the drill bit is off from a predetermined acceptable tolerance. In addition, if the drilling appears to be at or approaching the intended depth, the drill 50 may slow or stop to discontinue drilling.

Further exemplary embodiments may include a surgical saw including one or more micro- or miniature sensors associated therewith for use during a total knee arthroplasty procedure. Exemplary sensors may include individually or in combination, without limitation, inclinometers, accelerometers, magnetometers, and microgyroscopes. Each sensor is operatively coupled to a feedback device, such as a display system, to provide information to a surgeon regarding the position and/or orientation of the surgical saw. For instance, the surgeon may want to verify the depth of cutting to ensure that tissue damage outside of that expected does not occur. Exemplary components of a feedback device may include, without limitation, the display system introduced above, as well as an auditory feedback device such as an earpiece speaker. In each instance, the feedback device is designed to inform the surgeon regarding the position and/or orientation of the surgical instrument during surgery.

A third detailed exemplary application may include one or more micro- or miniature sensors associated with a surgical instrument and one or more micro- or miniature reference sensors associated with a selected anatomical feature to monitor the position of the instrument relative to the anatomical feature and possibly cease or slow operation of the instrument upon reaching a predetermined position relative to the anatomical feature. More detailed exemplary applications include total hip arthroplasty where one might prevent: (1) reaming too deep during acetabular preparation; (2) overpenetration during drilling of acetabular screw holes; (3) over-penetration during depth gauging of acetabular screw holes; (4) broaching too deep; and (5) inadequate reaming of the acetabulum.

Figure 6:
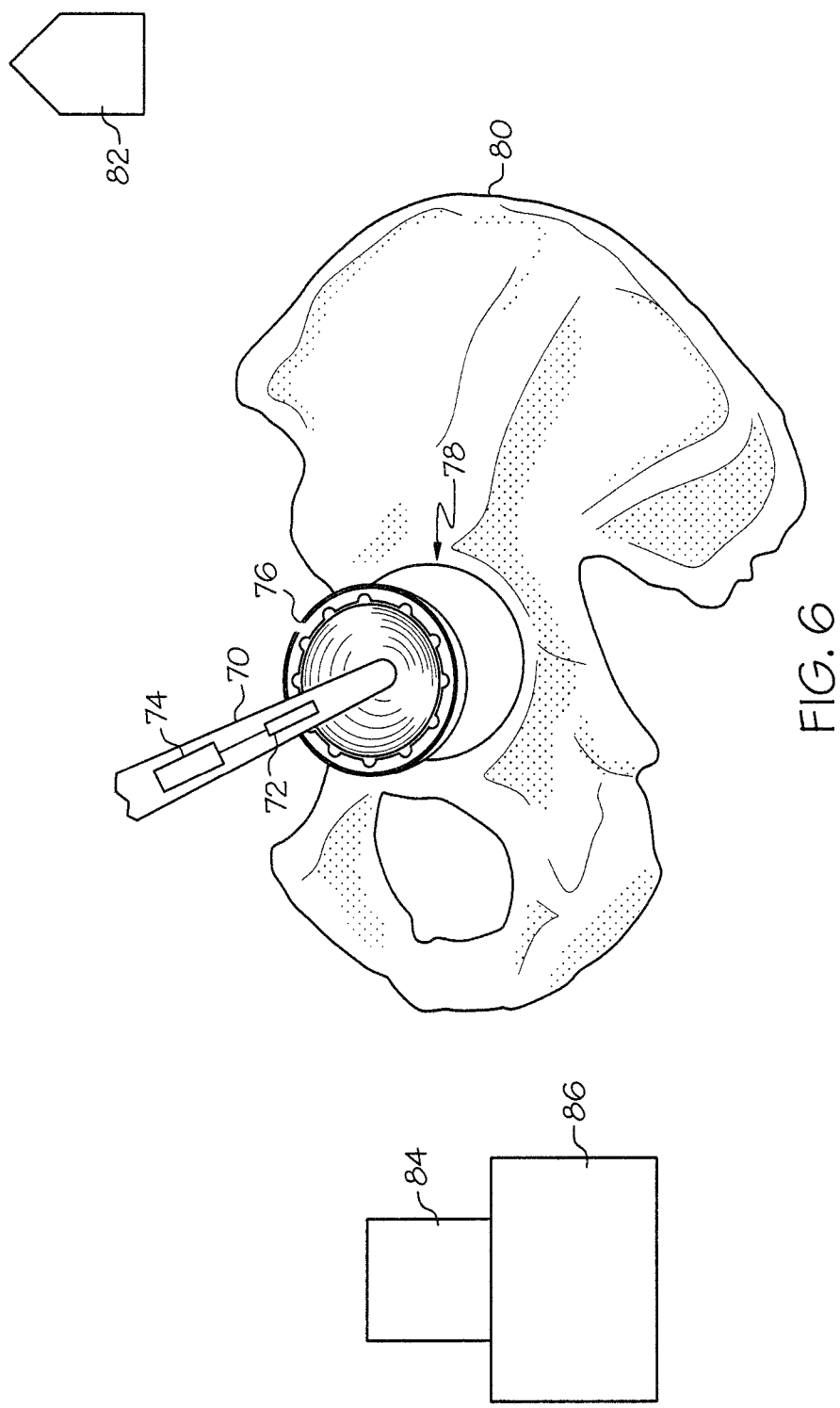
FIG. 6 is a representative and schematic view of an exemplary embodiment of the present invention.

Referencing FIG. 6, a surgical reamer 70 includes at least one magnetometer 72 operatively coupled to a transmitter 74 that may be carried by the reamer 70. A number of magnets 76 may be implanted circumferentially around an acetabulum 78 of a pelvis 80, where the magnets may have varying field strengths. The position of the reamer 70 may be measured in part using the earth's magnetic field, and more specifically, using the magnetic fields generated by the magnets 76 positioned about the acetabulum 78. Still further, an artificial magnetic field may be selectively created by a field generating device 82 to facilitate gauging the position of the reamer 70 independent of the pelvis 80. As the position of the reamer 70 in any of the three axes of movement is changed, the magnetometer 72 may detect the earth's magnetic field and/or the artificial magnetic field. The magnetometer 72 may be coupled to a data positioning device 84 capable of utilizing the magnetometer 72 output to discern the changes in position of the reamer 70. Those of ordinary skill in the art are aware of the practices through which magnetometers 72 may be used to monitor changes in position. In addition, the magnetometer 72 may likewise detect magnetic fields and field strengths associated with the magnets 74 to provide relevant magnetic field data to the positioning device 84 to calculate the relative position of the reamer 70 with respect to the magnets positioned around the acetabulum 78, and thereby the pelvis 80. The data positioning device 84 may be operatively coupled to a display or data readout 86 to enable the surgeon to reposition the reamer 70, based at least in part, upon the outputted data. In this manner, a surgeon may reposition and align the reamer 70 without requiring a direct line of sight. It is to be understood that other sensors may be used in place of the magnetometers and magnets to facilitate positioning and orienting the reamer 70 with respect to the acetabulum 78.

A further detailed exemplary application includes microgyroscopes mounted within the femoral broaches to determine the broach position within the femoral canal. In another detailed exemplary application, circular gyro rings are positioned distally along the femur to supplement the orientation and alignment of the broach within the femoral canal.

In a fourth detailed exemplary application, one or more micro- or miniature sensors are associated with a surgical instrument and one or more micro- or miniature reference sensors are associated with a surgical jig to monitor the position of the instrument with respect to the jig and possibly cease operation of the instrument upon reaching a predetermined position relative to the jig. Exemplary sensors to be associated with a surgical instrument include, without limitation, accelerometers, inclinometers, magnetometers, and gyroscopes. More detailed exemplary applications include: (1) ensuring that the saw is inserted and operative to a proper depth through a slot in the jig (no registration); (2) ensuring that the proper orientation (correct valgus/varus/slope) is achieved while cutting with a saw (with registration); and (3) ensuring proper drill penetration through an acetabular screw hole (independent of bone registration). Still further, exemplary sensors to be associated with a surgical jig include, without limitation, accelerometers, inclinometers, magnetometers, and gyroscopes. Exemplary positioning for the sensors associated with the jigs include, without limitation, within the guide rods of intramedullary femoral and tibial cutting jigs and/or extramedullary femoral and tibial cutting jigs to ensure that correct orientation exists between the saw and the jig prior to any bone being cut.

Figure 7:
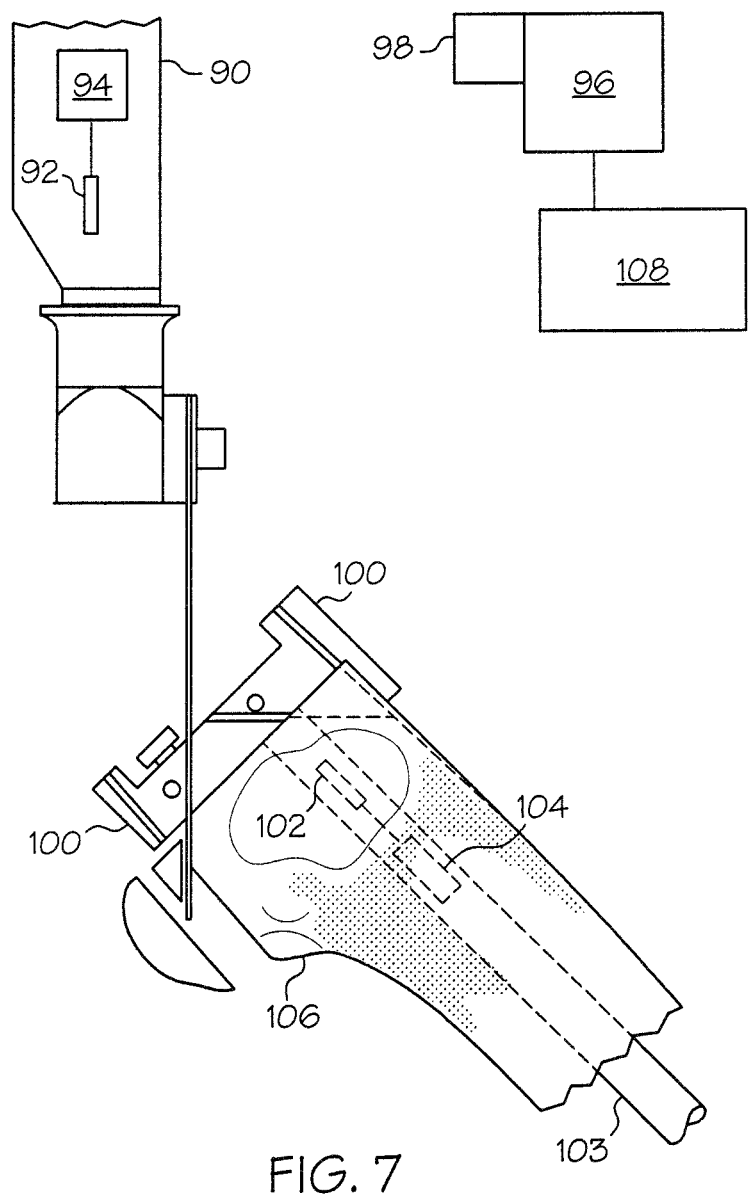
FIG. 7 is a representative and schematic view of an exemplary embodiment of the present invention.

Referencing FIG. 7, an exemplary embodiment may include a surgical saw 90 that includes one or more microsensors 92 associated therewith. The microsensors 92 may be coupled to a wireless transmitter 94 carried by the saw 90 or may simply include leads from the surgical saw 90 coupled to a data positioning device 96. When wireless transmitters 94 are utilized, a wireless receiver 98 may be included to capture the wireless signals and forward such data to the data positioning device 96. Likewise, a surgical knee jig 100 for use with a total knee arthroplasty procedure includes one or more microsensors 102, within the guide rod 103, coupled to a transmitter 104 associated therewith that output generated data that is received by the data positioning device 96. The surgical jig 100 is adapted to be mounted to the distal end of a femur 106 to prepare the distal end to accept a prosthetic femoral component (not shown). The data positioning device 96 utilizes the data from the microsensors 92, 102 to output data reflecting the relative position of the saw 90 with respect to the jig 100 that may be viewed by a surgeon on a visual display 108. Such data may be indicative of the depth of the cut as the position of the saw 90 changes with respect to the jig 100, thereby allowing the surgeon to know the depth of the cut without necessitating a direct line of sight. It will be understood by one of ordinary skill that the cuts made by the saw 90 do not require registration to bone, but instead utilize the relative position and/or orientation of the intramedullary guide rod 103. It is to be understood that the microsensors associated with the surgical jig 100 need not be identical in number and in function to those associated with the surgical saw 90.

In a fifth detailed exemplary application, one or more micro- or miniature reference sensors are associated with an anatomical feature and one or more micro- or miniature sensors are associated with a medical instrument adapted to position a prosthetic device. The sensors allow for the monitoring of the position of the prosthetic device with respect to the anatomical feature to ensure proper alignment of the prosthetic device. It is within the scope of the invention that anatomical features include, without limitation, bone, muscle, tendons, ligaments, and skin. In instances where a small incision is made and other internal landmarks may not be apparent, a combination of sensors on an anatomical feature and a medical instrument may assist in accurate placement of a prosthetic component without necessitating a direct line of sight.

Figure 8:
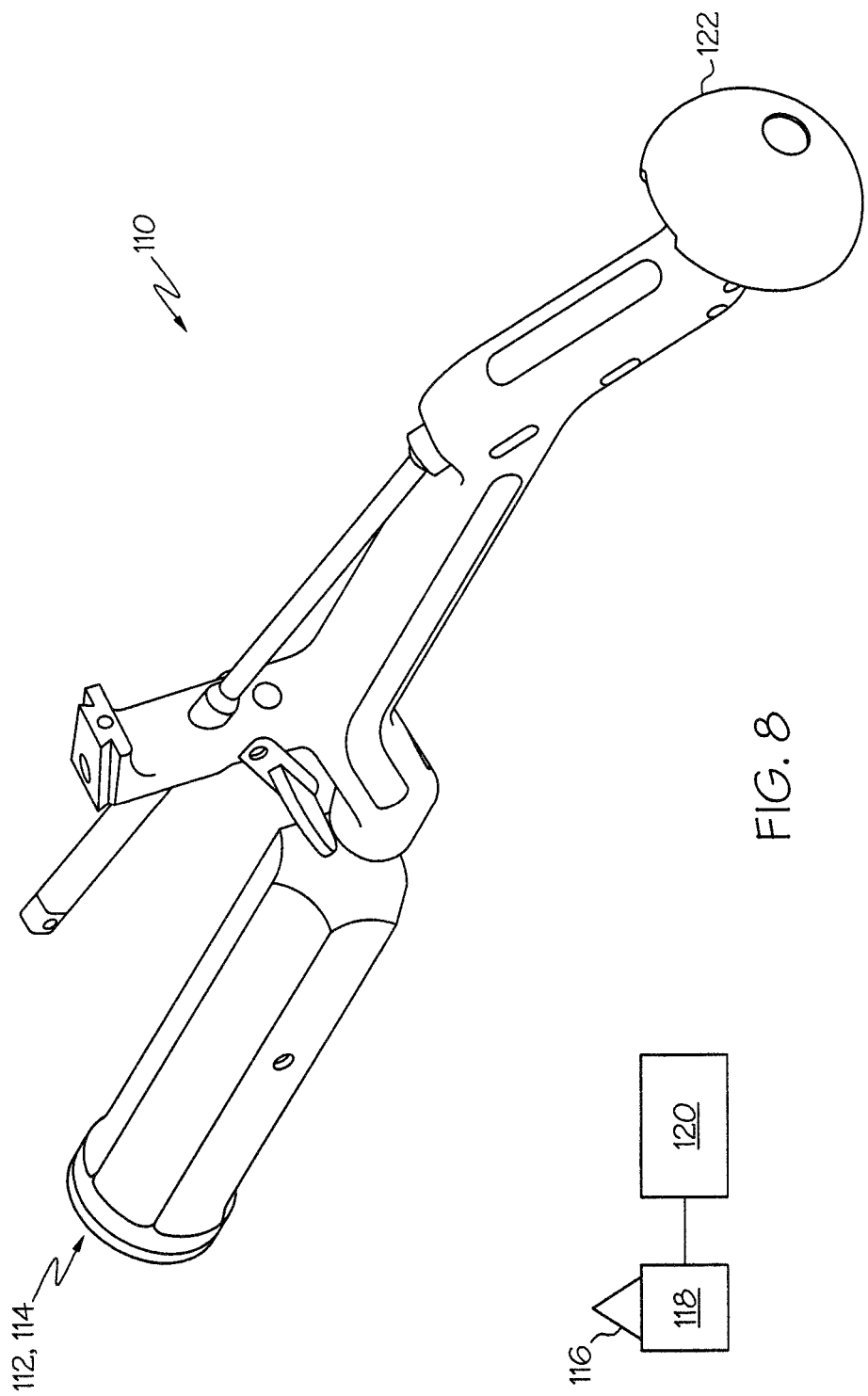
FIG. 8 is a representative and schematic view of an exemplary embodiment of the present invention.

Referencing FIG. 8, a surgical cup inserter 110 includes at least one microgyroscope 112 operatively coupled to a wireless transmitter 114 that may be carried within the handle of the inserter 110. The microgyroscope 112 may be capable of sensing changes in movement in all three axes of movement and, via the transmitter 114, disseminating such position data to a remote receiver 116. The remote receiver 116 is operatively coupled to a data positioning device 118 adapted to utilize the microgyroscope 112 output data to determine the relative position of the inserter 110 with respect to an anatomical feature (not shown). In an exemplary form, the anatomical feature may include the pelvis having one or more sensors mounted thereto that are operatively coupled to the data positioning device 118. Such sensors may be wired or wireless and include wireless transmitters where applicable. In an exemplary process, the pelvis (not shown) includes sensors positioned approximate the acetabulum to provide reference data in at least one dimension and a reference point for comparative analysis of the position data output by the microgyroscope 112. As such, the data positioning device 118 is able to calculate the position of the inserter 110 with respect to the pelvis, even as the position of the inserter 110 changes with respect to the pelvis. The data positioning device 118 may be operatively coupled to a display monitor 120 to display the relative position of the inserter 110 with respect to the pelvis, including the angle of insertion of the prosthetic cup 122 within the acetabulum. This angle data may allow the surgeon to compare the current angle with a predetermined angle (which may have been calculated preoperatively using one or more X-rays or other position determining devices) and guide placement of the prosthetic cup into the correct abduction and anteversion orientation with respect to the acetabulum.

Figure 9:
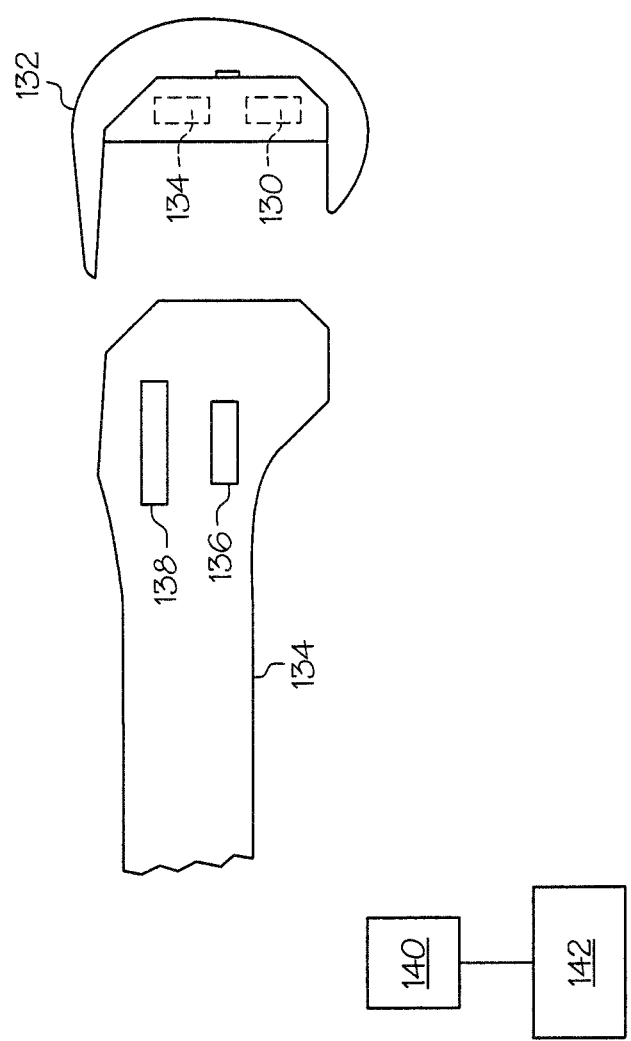
FIG. 9 is a representative and schematic view of an exemplary embodiment of the present invention.

Referring to FIG. 9, a sixth detailed exemplary application may include one or more micro- or miniature sensors 130 mounted inside a prosthetic trial component 132 to identify if the trial component is oriented correctly with respect to an anatomical feature 134. More specifically, the prosthetic trial component, or femoral knee trial prosthesis 132, includes one or more sensors 130 associated therewith that sense changes in orientation in free space and output such data to a wireless transmitter 134 within the trial 132. The anatomical feature, or femur 136, includes micro- or miniature sensors 138 mounted thereto during a total knee arthroplasty procedure. The outputs of the sensors 138 may be coupled to a wireless transmitter (not shown) or may be coupled directly to a data position device 140 also receiving inputs indirectly from the micro- or miniature sensors 130 within the femoral knee prosthesis 132. A visual display 142 may be operatively coupled to the data positioning device 140 to provide a visual representation, capable of rotation in three space, to enable the surgeon to see what cannot be seen via a direct line of sight.

Figure 10:
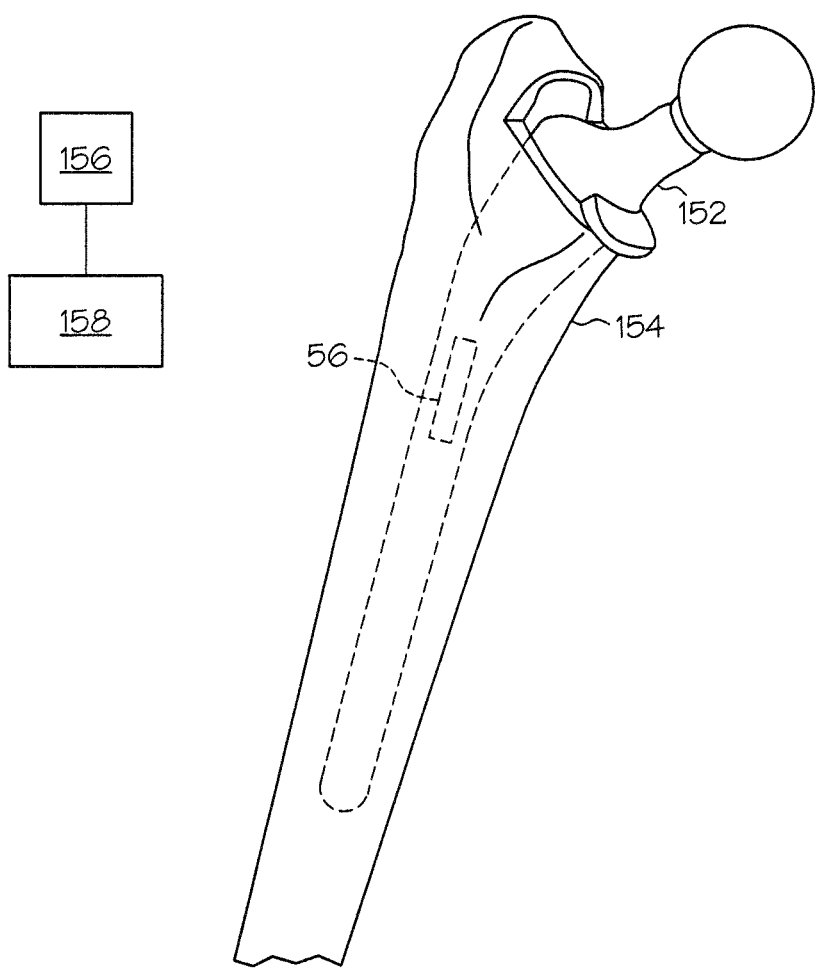
FIG. 10 is a representative and schematic view of an exemplary embodiment of the present invention.

Referencing FIG. 10, an alternate exemplary embodiment of the sixth aspect may include one or more micro- or miniature sensors (not shown) mounted inside a prosthetic trial component 152 to identify if the trial component is oriented correctly with respect to an anatomical feature 154. More specifically, the prosthetic trial component, or femoral hip trial prosthesis 152, includes one or more sensors associated therewith that sense changes in orientation in free space and output such data to a wireless transmitter (not shown) within the trial component 152. The anatomical feature, or femur 154, includes a micro- or miniature sensor 156 mounted thereto during a total hip arthroplasty procedure. The output of the sensor may be coupled to a wireless transmitter (not shown) or may be coupled directly to a data position device 156 also receiving inputs indirectly from the micro- or miniature sensors within the femoral hip trial prosthesis 152. A visual display 158 may be operatively coupled to the data positioning device 156 to provide a visual representation, capable of rotation in three space, to enable the surgeon to see what cannot be seen via a direct line of sight. More specifically, the orientation of the trial component 152 may be monitored to verify that the trial component is within the femoral canal in varus or valgus. Still further, the relative anteversion of the stem of the femoral hip trial 152 may also be determined.

In still a further exemplary application, one or more micro- or miniature sensors may be mounted to trial prosthetic components to provide relevant data to optimize range of motion of the prosthetic joint by selecting final prosthetic components that mitigate dislocation tendencies. In addition, such trial prosthetic components may provide relevant data regarding ligament balance and joint kinematics function testing relevant to final prosthetic component selection.

In a seventh detailed exemplary application, one or more micro- or miniature sensors may be mounted to a prosthetic trail component. Prosthetic trail components are utilized by a surgeon to verify the relevant dimensions of the eventual prosthetic component to be implanted. In addition to sensing three dimensional positional data, such sensors may measure absolute values and range of motion to discern which prosthetic components fit best in a particular patient. Such measurements may also be compared to the position of one or more anatomical features, such as bone, where the bone has a micro- or miniature reference sensor mounted thereto or in proximity thereto. Such prosthetic components may be used with or without registration and may be utilized in a wide range of surgical procedures beyond total hip arthroplasty and total knee arthroplasty.

Figure 11:
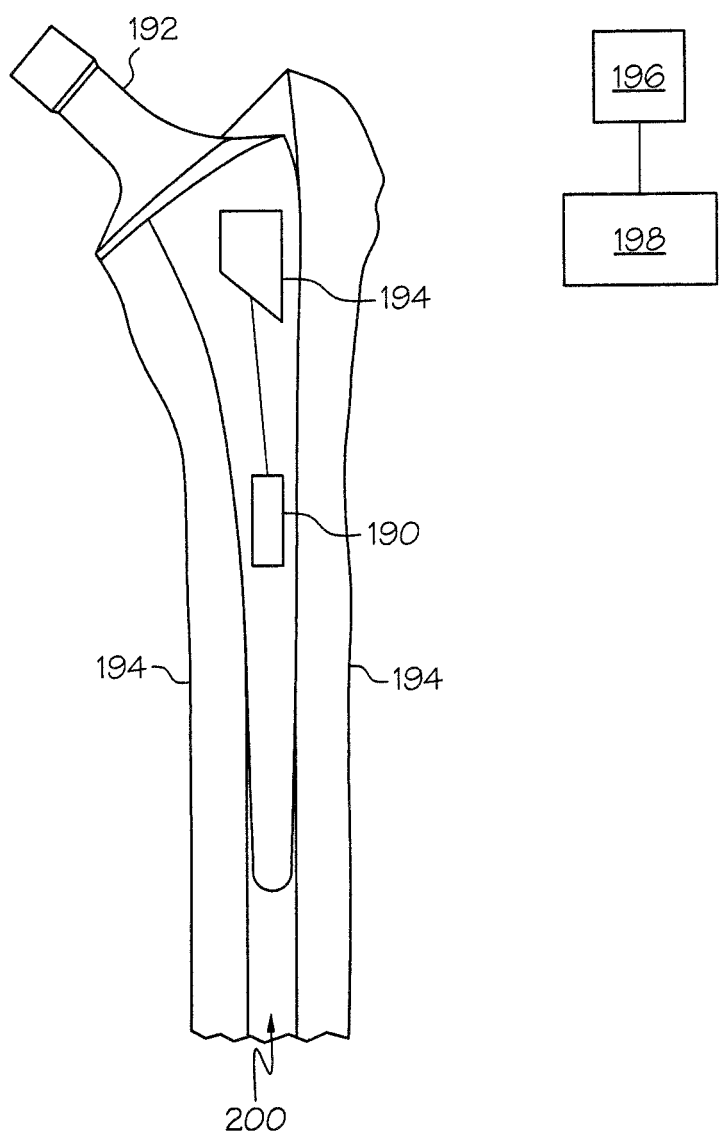
FIG. 11 is a representative and schematic view of an exemplary embodiment of the present invention.

Referencing FIG. 11, a seventh exemplary application may include one or more micro- or miniature sensors 190 mounted inside a prosthetic trial component 192 to provide feedback regarding the orientation of the trial component 192 during a total hip arthroplasty procedure. More specifically, the prosthetic trial component, or femoral hip trial prosthesis 192, includes one or more sensors 190 associated therewith that sense changes in position and/or orientation in free space and output such data to a wireless transmitter 194 within the prosthesis 192 while the trial is repositioned with respect to the femur 194. A data position device 196 receives signals from the transmitter 194 and calculates the position of the prosthesis 192 and any changes in position in real-time. Visual representation regarding the orientation of the prosthesis 192 may be shown on a visual display 198 operatively coupled to the data position device 196. The visual display 198 may be programmed to concurrently show the position of the prosthesis 192 and the position of the patient's bone from preoperative X-rays or other data that effectively show the relative anatomical position of the patient. More specifically, the orientation of the trial 192 may be monitored to verify that the trial 192 is within the femoral canal 200 in varus or valgus. Still further, the relative anteversion of the stem of the femoral trial 192 may also be determined.

Figure 12:
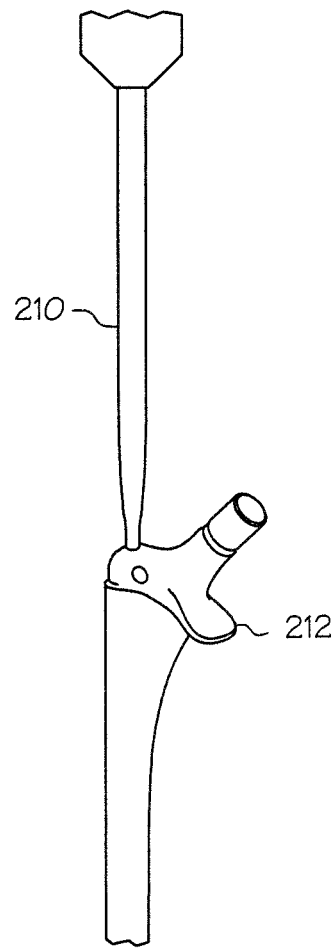
FIG. 12 is a representative view of an exemplary embodiment of the present invention.

Referencing FIG. 12, in a further detailed exemplary application, a surgical instrument 210 and prosthetic trial component 212 each have micro- or miniature sensors (not shown) associated therewith to provide guidance to maneuver the instrument 210 and trial 212 for insertion, impaction, and/or extraction of the trial 212. More specifically, the surgical instrument may include a surgical stem inserter 210 having a threaded end adapted to be received within an opening on the shoulder of a trial femoral prosthetic component 212. As discussed in a previous exemplary application, such an exemplary surgical instrument and exemplary prosthetic trial component may be useful in minimally invasive surgery where direct line of sight may not continuously be possible. Still further, such an exemplary surgical instrument and exemplary prosthetic trial component may be particularly useful in targeting and facilitate coupling and disengagement between the trials and surgical instruments without necessitating a direct line of sight or an unduly large incision.

Figure 13:
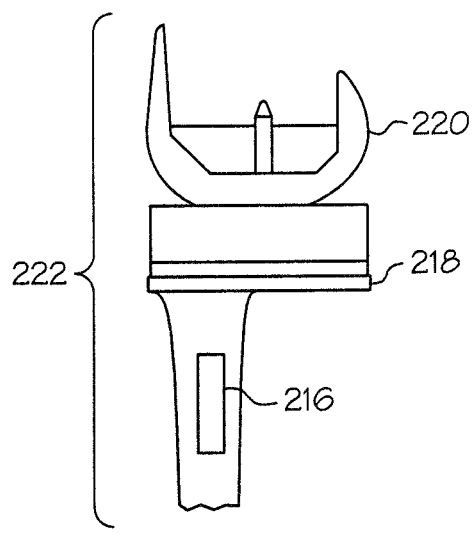
FIG. 13 is a representative view of an exemplary embodiment of the present invention.

Referring to FIG. 13, an eighth detailed exemplary application may include one or more micro- or miniature sensors 216 mounted to a tibial tray prosthetic device 218 to provide positional and/or orientational information sufficient to discern if subsidence is occurring subsequent to total knee arthroplasty. Still further, one or more micro- or miniature sensors (not shown) may be mounted on a femoral prosthetic device 220 to provide positional and/or orientational information sufficient to discern if the prosthetic knee joint 222 and the range of motion associated therewith are within proper tolerances. Such information could be compared to data generated during prosthetic trial fittings, where the prosthetic trials included one or more micro- or miniature sensors, to verify that the final prosthetic components are mimicking the final prosthetic trial components on which the surgeon based the choice of final prosthetic components.

In a further detailed exemplary application, the position and depth of a femoral prosthetic shaft within the femoral canal could be monitored over time to determine if subsidence or loosening was occurring after a total hip arthroplasty procedure.

In a ninth detailed exemplary application, one or more micro- or miniature sensors may be mounted to a prosthetic device or surgical retainer. A further detailed exemplary application includes associating one or more micro- or miniature sensors along an outer rim of a prosthetic cup to facilitate aligning and orienting the cup within the acetabulum. An additional exemplary embodiment includes one or more microgyroscopes placed within a femoral component trial to provide relevant data to determine varus and valgus and flexion and extension alignment relative the center of the femoral canal. An even further exemplary use may include mounting a micro- or miniature sensor to both the acetabulum and femoral component trials (in the femoral neck or in the femoral head) to discern the relative stability (range of movement (ROM) and angle of dislocation) between the two components.

Figure 14:
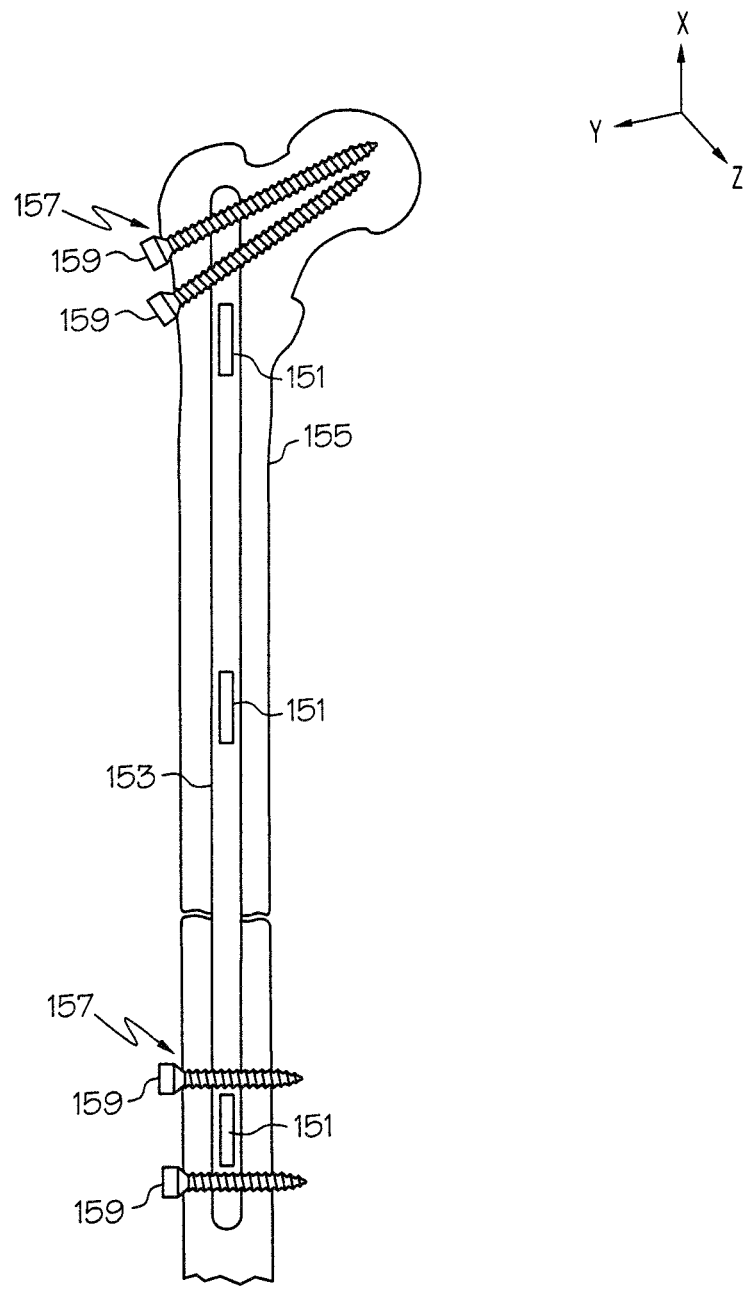
FIG. 14 is a representative view of an exemplary embodiment of the present invention.
Figure 15:
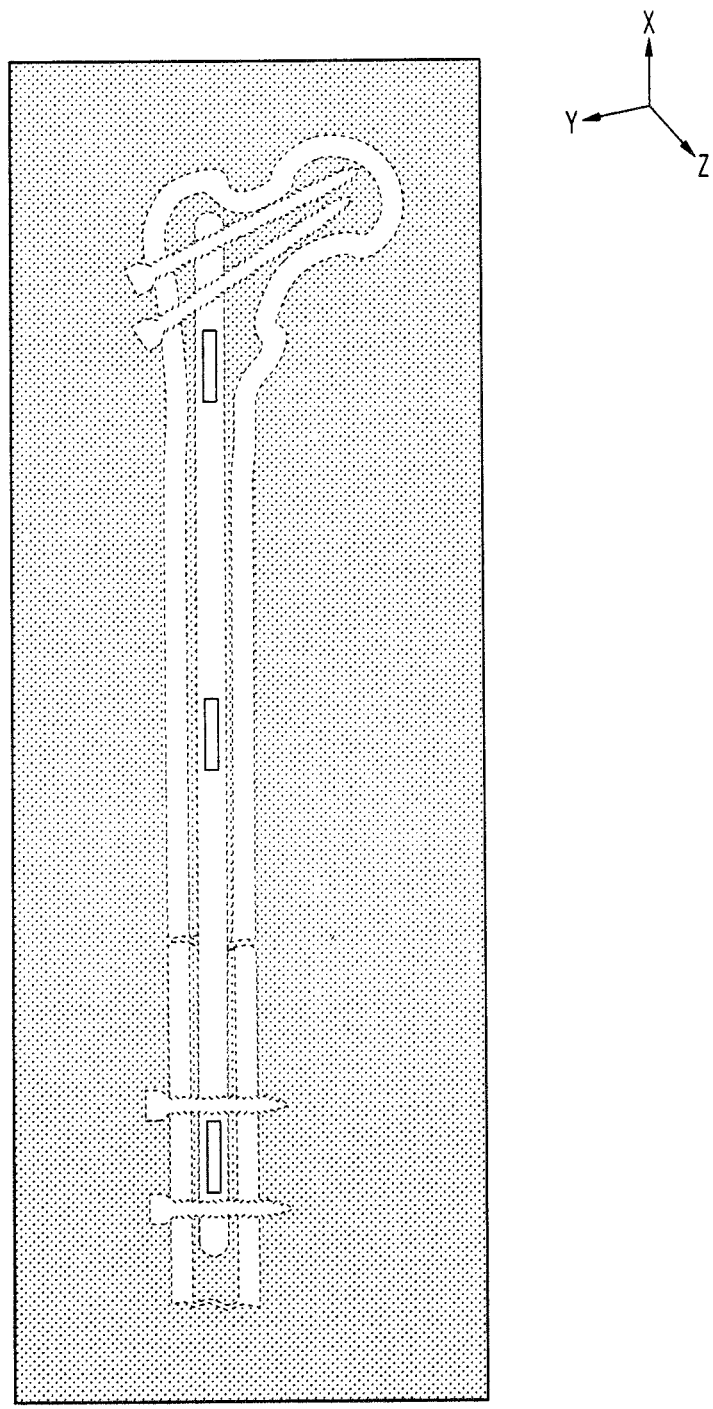
FIG. 15 is an X-ray taken of the representative view of FIG. 14.

Referencing FIGS. 14 and 15, a femoral rod 153 for use in repair of a fractured femur 155 may include one or more micro- or miniature sensors 151 associated therewith. The rod 153 includes a plurality of holes 157 therethrough that are adapted to receive screws 159 to mount the rod 153 to the femur 155. However, before the screws 159 are introduced therein, a corresponding hole must be drilled through the femur 155 that is precisely aligned with one of the holes of the rod 153. One challenge to surgeons has been discerning the position and orientation of the holes 157, then maintaining the position and orientation of holes 157 while drilling through the femur 155. Prior art techniques involved X-ray machines that were cumbersome and hindered the range of motion of the surgeon. The present invention, however, does not necessitate use of cumbersome X-ray machines, but relies upon the sensor or sensors 151 associated with the rod 153 to discern the position of the holes therethrough. Exemplary sensors 151 may include individually or in combination, without limitation, inclinometers, accelerometers, magnetometers, and microgyroscopes. The sensor 151 may be coupled to a micro- or miniature transmitter device to transmit sensor data regarding the position and/or orientation of the rod 153 in three axes of movement, represented by planes X, Y, and Z. A wireless receiver, operatively coupled to a display system, receives the signals broadcast by the transmitter and forwards the data derived from the signals for display upon the system. The display system is designed to provide feedback for the surgeon regarding the position and/or orientation of one or more holes within the rod 153.

In a further exemplary application, a surgical drill may include one or more micro- or miniature sensors associated therewith, along with a femoral rod that includes one or more micro- or miniature sensors associated therewith for use in repair of a fractured femur. As discussed above, the rod includes a plurality of holes therethrough that are adapted to receive screws to mount the rod to the femur. The sensors associated with the rod provide position and/or orientation data regarding the holes through the rod, while the sensors associated with the drill provide position and/or orientation data regarding the position and/or orientation of the drill bit to align the drill bit with the holes in the rod without necessitating a direct line of sight prior to commencing the drilling. As discussed above, utilizing positional and/or orientational sensors alleviates the reliance upon cumbersome X-ray equipment.

In still a further exemplary application, one or more micro- or miniature sensors may be mounted to a prosthetic component to provide relevant data regarding the range of motion available to the patient. In addition, prosthetic components having one or more micro- or miniature sensors associated therewith may be compared against data generated by trial prosthetic components to compare the range of motion available to the patient. Still further, such prosthetic components may provide relevant data regarding ligament balance and joint kinematics function testing prior to termination of the surgical procedure. Even further, such prosthetic components may include sensors capable of generating positional and/or orientational data such that ligament balance and joint kinematics function can be assessed and compared to previous measurements to discern what, if any, changes have occurred over time.

Figure 16:
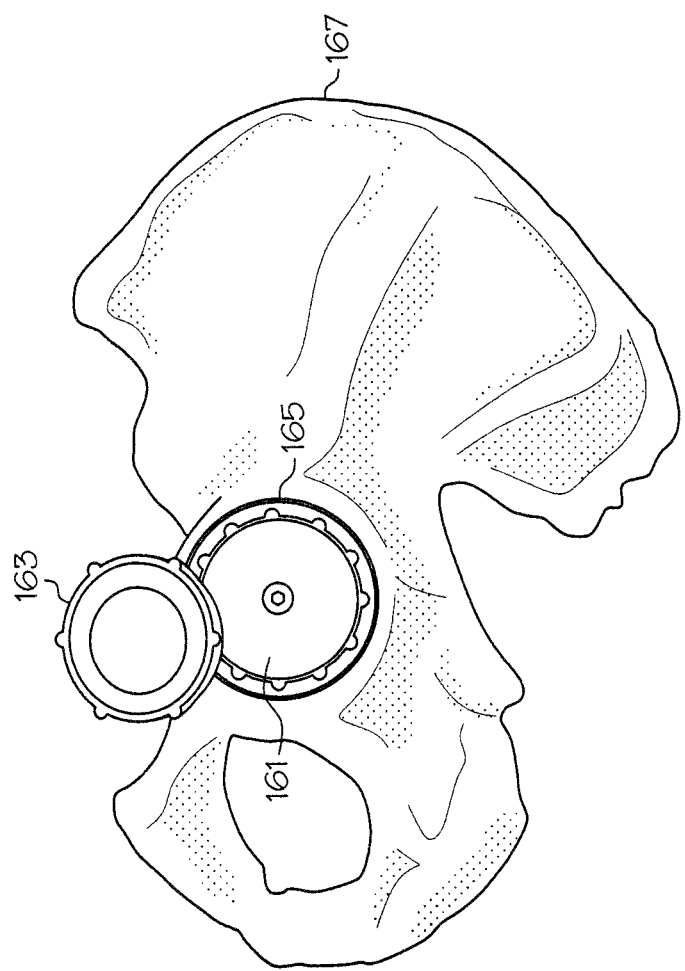
FIG. 16 is a representative view of an exemplary embodiment of the present invention.

Referencing FIG. 16, a tenth detailed exemplary application may include one or more micro- or miniature sensors mounted to a screw cap dome screw 161 to identify the position of a final prosthetic hip component. In one exemplary application, the screw cap dome screw 161 provides feedback regarding the orientation of the insert 163 within the cup 165 secured to the pelvis 167 to ensure that the insert 163 is adequately impacted and adjacent to the cup 165. In another exemplary application, the sensors may provide position and/or orientation data over time that may be detected and recorded to discern if one or more of the final prosthetic hip components have graduated in position and/or orientation over time.

In an eleventh detailed exemplary application, one or more micro- or miniature reference sensors are associated with an anatomical feature and one or more micro- or miniature sensors are associated with a prosthetic device. The sensors allow for the monitoring of the position of the prosthetic device with respect to the anatomical feature to track changes in the relationship between the prosthetic device and the anatomical feature over time. More specifically, the anatomical feature may include a patient's femur and the prosthetic device may include a femoral stem for use in a total hip arthroplasty procedure. Still further, the anatomical feature might comprise a patient's tibia and the prosthetic device may include a tibial tray for use in a total knee arthroplasty procedure.

Figure 17:
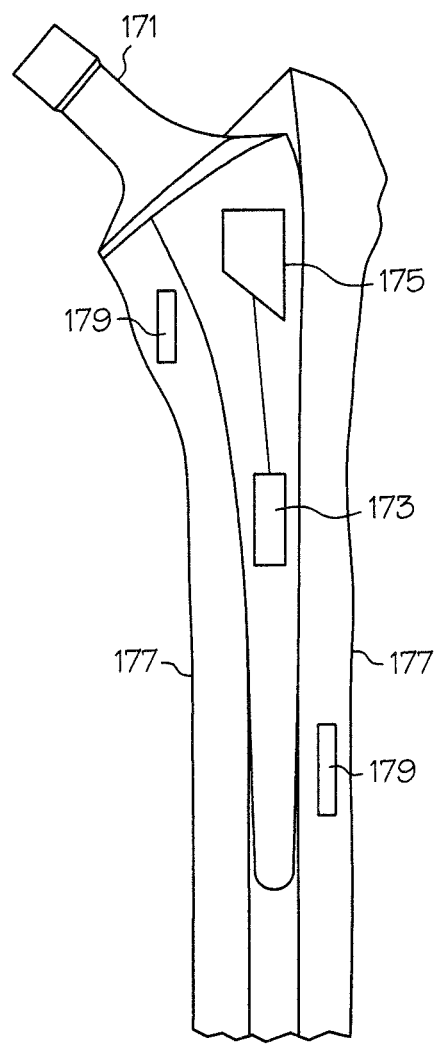
FIG. 17 is a representative view of an exemplary embodiment of the present invention.

Referencing FIG. 17, a femoral prosthetic component 171 includes at least one or more micro- or miniature reference sensors 173 operatively coupled to a wireless transmitter 175. The sensor 173 may be capable of sensing changes in movement in all three axes of movement and, via the transmitter 175, disseminating such position data to a remote receiver. The remote receiver may be operatively coupled to a data positioning device adapted to utilize the sensor 173 output data to determine the relative position of the femoral prosthetic component 171 with respect to an anatomical feature, such as, without limitation, a patient's femur 177. In an exemplary form, the femur 177 may include one or more sensors 179 mounted thereto that are operatively coupled to the data positioning device. Such sensors may be wired or wireless and include wireless transmitters where applicable. In an exemplary process, the sensors 179 associated with the femur 177 provide reference data in at least one dimension and a reference point for comparative analysis of the position and/or orientation data output by the sensors 173 associated with the femoral prosthetic component 171. As such, the data positioning device is able to calculate the position of the femoral prosthetic component 171 with respect to the femur 177, even as the position of the prosthetic component 171 changes with respect to the femur 177. The data positioning device may be operatively coupled to a display monitor to display the relative position of the prosthetic component 171 with respect to the femur 177, including the angle of insertion of the prosthetic component 171 within the femur 177. This angle data may allow the surgeon to compare the current angle with a predetermined angle (which may have been calculated preoperatively using one or more X-rays or other position determining devices) and guide placement of the prosthetic component into the correct position.

In a twelfth detailed exemplary application, one or more micro- or miniature reference sensors are associated with an implant, independent of a prosthetic or trial component, a surgical device, or a surgical jig. The implant may be positioned within an anatomical feature, such as, without limitation, the femoral canal. Likewise, the implant may be positioned adjacent to an anatomical feature, such as without limitation, the femoral bone. By using an implant with one or more micro- or miniature reference sensors, a point of reference may be established that is relatively fixed over time and in proximity to the area in which the surgeon is concerned.

Figure 18:
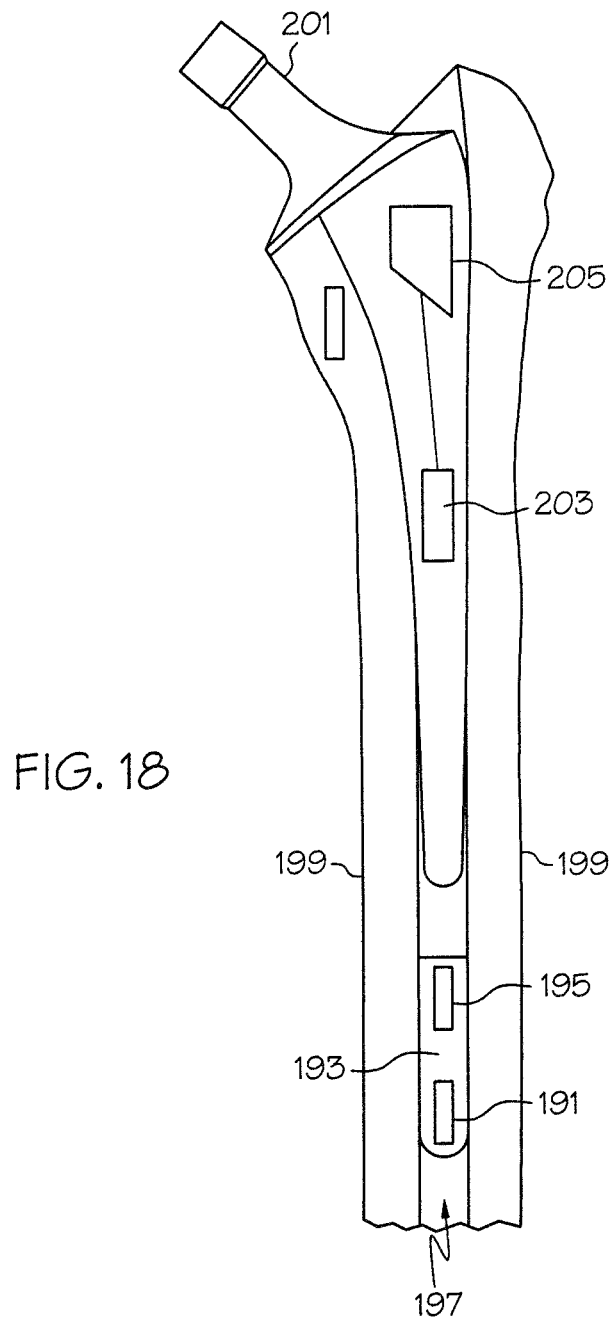
FIG. 18 is a representative view of an exemplary embodiment of the present invention.

Referencing FIG. 18, an exemplary application may include one or more micro- or miniature sensors 191 associated with an implant 193. Exemplary sensors 191 may include individually or in combination, without limitation, inclinometers, accelerometers, magnetometers, and microgyroscopes. The sensor 191 may be coupled to a micro- or miniature transmitter device 195 to transmit sensor data regarding the position and/or orientation of the implant 193 in three axes of movement. A wireless receiver, operatively coupled to a display system, receives the signals broadcast by the transmitter 195 and forwards the data derived from the signals for display upon the system. The display system is designed to provide a reference point for the surgeon regarding the position and/or orientation of one or more surgical instruments, final and trial prosthetic components, and surgical jigs used during a surgical procedure.

In a further exemplary embodiment, the implant 193 is inserted into a femoral canal 197 of a patient's femur 199 during a total hip arthroplasty procedure. In such an exemplary embodiment, a prosthetic femoral component 201 likewise includes one or more micro- or miniature sensors 203 associated therewith and in communication with a wireless transmitter 205 that provides relevant data regarding the position of the femoral component 201. Likewise, the implant 193 may provide relevant data that is imputed to the position and/or orientation of a patient's femur 199. In this manner, the surgeon can precisely make one or more cuts with a surgical saw (not shown) concerning the proximal portion of the patient's femur 199 prior to insertion of the prosthetic component 201. In addition, when the prosthetic component 201 is ready for insertion, the surgeon may leave the implant 193 in place and may utilize the position data from the sensors 191 as a point of reference for positioning and orienting the prosthetic component 201.

It is also within the scope of the present invention to replace one or more of the reference sensors with transmitting devices, such as, without limitation, magnets. In this manner, the signal or field generated may be detected by one or more reference sensors, such as, without limitation, magnetometers. Likewise, other transmitting devices and sensors, such as piezoelectric sensors, known to those of ordinary skill will likewise fall within the scope of the present invention.

While some of the aforementioned exemplary embodiments have been discussed with respect to total hip arthroplasty or total knee arthroplasty, the same principles and advantages are likewise applicable for other medical procedures where microgyroscopes or other sensors may be mounted to one or more surgical devices, anatomical features, implants, and prosthetic components to ensure that the object is oriented properly with respect to one or more points of reference.

Current technology in reference sensors such as that disclosed in United States Patent Application Publication Nos. 2002/0180306 and 2002/0104376, the disclosures of which are hereby incorporated by reference, evidences substantial development in reducing the size of such sensors utilizing nanotechnology.

The exemplary sensors discussed herein and adapted for use with the present invention may fall within generally two classes: source and sourceless. Source sensors rely on artificial stimuli such as generated magnetic fields or outputs from other artificial devices for one or more points of reference. In exemplary form, a pair of source sensors may rely on each other for relative points of reference. In a further exemplary form, a first sensor may be mounted to a first object and a reference sensor may be mounted to a second object, where the first sensor utilizes a magnetic field or other output generated by the reference sensor to provide a reference point as to the movement of the second sensor with respect to the first sensor. Likewise, the reference sensor may utilize a magnetic field or other output from the first sensor as a reference point as to the movement of the reference sensor with respect to the first sensor. In this manner, a surgeon is able to manipulate a first object having the first sensor mounted thereto with respect to the second object with the second sensor mounted thereto without necessitating a direct line of sight to position the first object in relation to the second object.

A second class of sensors, sourceless sensors, relies on natural or ever-present stimuli such as the earth's magnetic field or gravity. Exemplary sourceless sensors may utilize the magnetic field and/or gravity of the earth to provide a fixed reference point for measurements such as tilt and level. Such sensors may be self-contained and, unlike some source sensors, do not require a transducer to create an artificial stimulus or field.

Figure 19:
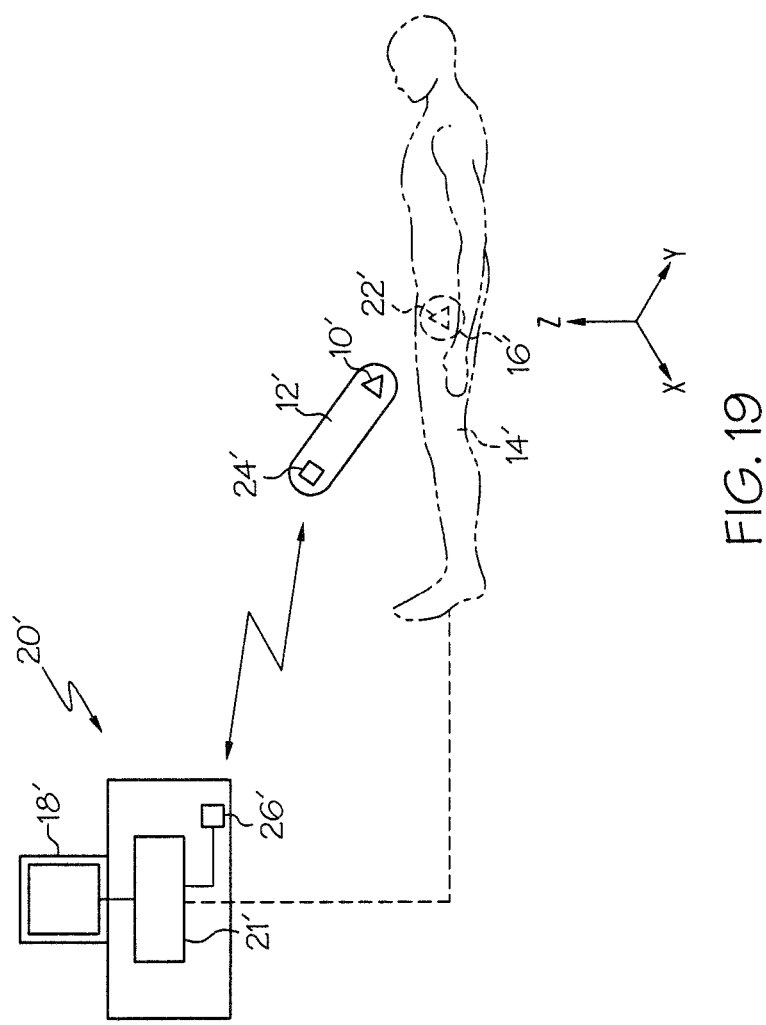
FIG. 19 is a schematic representation of an alternate exemplary embodiment of the present invention.

As shown in FIG. 19, a first exemplary sensor technology available for use with the present invention is the Flock of Birds, and more specifically, the microBIRD technology commercially available from Ascension Technology Corporation (see http://www.ascension-tech.com/products/microbird.php), and patented in U.S. Pat. Nos. 4,849,692 and 4,945,305, the disclosures of which are incorporated herein by reference. Flock of Birds is a magnetic-transducing technique that measures the position and orientation of one or more receiving antenna sensors 10' located on the surgical device, tool, prosthetic component, or implant 12' with respect to a transmitter 22' located on a reference object 16'. The transmitter 22' includes three individual antennae arranged concentrically to generate a multiplicity of DC magnetic fields that are picked up by the sensor 10'. The sensor measures the position and orientation of the object 16' which carries it. The sensor 10' consists of three axes of antenna that are sensitive to DC magnetic fields. The transmitter 22' includes a driver that provides a controlled amount of DC current to each axis of the transmitter. Both the sensor 10' and the transmitter 22' driver may be modified in the present invention to facilitate wireless communication with the display system 20'. The display system 20' controls the amount of DC current provided by the transmitter 22' driver to the transmitter 22' axis. The signal output from the sensor 10' is transmitted back to the conditioning hardware and software 21' of the display system 20', which conditions and processes the signal to compute position and orientation of the sensor 10' with respect to the transmitter 22' using the Flock of Birds available algorithms. Such position and orientation data is then used to generate a visual signal to be displayed on the visual display 18'.

Figure 20:
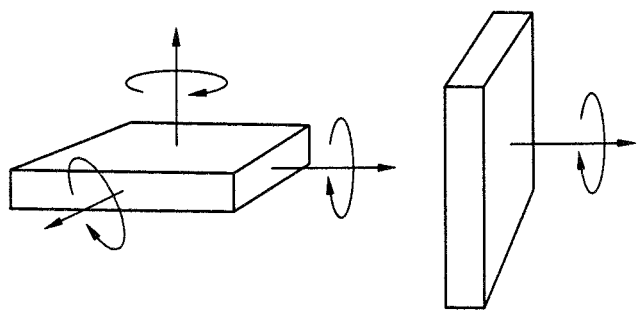
FIG. 20 is a representation illustrating movements of a body for sensing by a gyroscope sensor according to an exemplary embodiment of the present invention.

A second exemplary sensor technology for use with the present invention may include microgyroscopes to measure angular rate; i.e., how quickly an object turns. The rotation is typically measured with reference to one of three axes: X, Y, and Z or yaw, pitch, and roll. A microgyroscope with one axis of sensitivity can also be used to measure other axes by mounting the microgyroscope differently, as shown in FIG. 20. Here, a yaw-axis microgyroscope is mounted on its side so that the yaw axis becomes the roll axis. Depending on how a microgyroscope is mounted, its primary axis of sensitivity can be one of the three axes of motion: yaw, pitch, or roll.

Exemplary microgyroscopes for use with the present invention include ADXRS150 available from Analog Devices (http://www.analog.com). Such exemplary microgyroscopes are rotational rate measurement systems on a single monolithic integrated circuit. The exemplary microgyroscopes measure angular rate by means of Coriolis acceleration. Each of three microgyroscopes may be oriented with respect to the surgical device, tool, prosthetic component, or implant so that each of the X, Y, and Z planes is accommodated.

One practical application is to measure how quickly a surgical instrument is turned by mounting one or more microgyroscopes thereto. In addition, the angular rate can be integrated over time to determine angular position. For example, if a microgyroscope senses that the surgical instrument is out of position, an appropriate signal may indicate such to the surgeon and discontinue operation of the instrument until the instrument is oriented in a proper manner.

Figure 21:
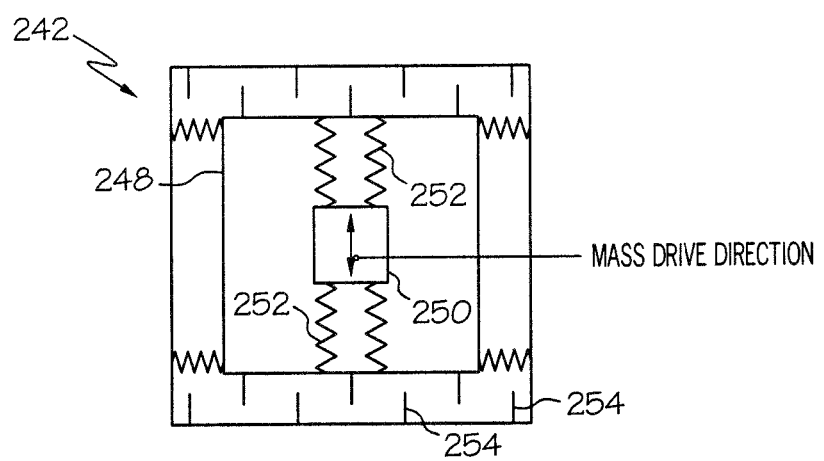
FIG. 21 is a schematic representation of a gyroscope sensor for use with an exemplary embodiment of the present invention.

Referencing FIG. 21, an exemplary microgyroscope 242 includes a frame 248 containing a resonating mass 250 tethered to a substrate by springs 252 at 90.degree. relative to the resonating motion to measure the Coriolis acceleration. A plurality of Coriolis sense fingers 254 are used to capacitively sense displacement of the frame in response to the force exerted by the mass. If the springs 252 have a stiffness, K, then the displacement resulting from the reaction force will be 2 .OMEGA.vM/K. As the rate of rotation with respect to the microgyroscope 242 increases, so does the displacement of the mass 250 and the signal derived from the corresponding capacitance change. It should be noted that the microgyroscope 242 may be mounted anywhere on the surgical device, tool, prosthetic component, or implant and at any angle, so long as the sensing axis of the microgyroscope 242 is parallel to the axis of rotation. The microgyroscopes 242 measure the displacement of the resonating mass 250 and its frame 248 due to the Coriolis effect through capacitive sensing elements attached to a resonator. Displacement due to angular rate induces a differential capacitance in this system. If the total capacitance is C and the spacing of the sense fingers 254 is "g", then the differential capacitance is 2 .OMEGA.vMC/gK, and is directly proportional to the angular rate. The fidelity of this relationship is excellent in practice, with nonlinearity less than 0.1%.

The microgyroscopes 242 can sense capacitance changes as small as 12.times.10.sup.−21 farads (12 zeptofarads) from deflections as small as 0.00016 Angstroms (16 femtometers). This can be utilized in the surgical device, tool, prosthetic component, or implant by situating the electronics, including amplifiers and filters, on the same die as the gyroscope 242. The differential signal alternates at the resonator frequency and can be extracted from the noise by correlation.

The exemplary ADXRS microgyroscopes 242 employ two resonators that operate anti-phase to differentially sense signals and reject common-mode external accelerations that are unrelated to angular motion to angular rate-sensing that makes it possible to reject shocks of up to 1,000 g. As a result, the microgyroscopes 242 measure the same magnitude of rotation, but give outputs in opposite directions. Therefore, the difference between the two outputs is used to measure angular rate. This cancels non-rotational signals that affect both ends of the microgyroscope 242.

Accelerometers may also be utilized as sensors 10, 10' in the present invention to measure tilt or inclination, inertial forces, and shock or vibration. An intended application for accelerometers with respect to the present invention includes measuring tilt in at least one axis and exemplary accelerometers are available as model ADXL203BE from Analog Devices (http://www.analog.com). Such exemplary accelerometers are acceleration measurement systems on a single monolithic integrated circuit to implement an open loop acceleration measurement architecture. It is envisioned that the accelerometer be oriented with respect to the surgical device, tool, prosthetic component, or implant so the accelerometer's X and Y axis would most often approach a parallel orientation with respect to the earth's surface. In such an orientation, tilt may be measured in two axes for roll and pitch. In addition to measuring acceleration, the acceleration may be integrated over time to provide velocity data, which can likewise be integrated over time to provide position data. Those of ordinary skill are familiar with the noise considerations associated with power supplies for sensors, and in particular, accelerometers. It is within the scope of the invention to utilize a capacitor, generally around 1 .mu.F, to decouple the accelerometer from the noise of the power supply. Other techniques may include adding a resistor in series with the power supply or adding a bulk capacitor (in the 1 .mu.F to 4 .mu.F range) in parallel with the first capacitor (1 .mu.F).

Other exemplary accelerometers include model KXG20-L20 available from Kionix, Inc. (http://www.kionix.com), model SCA610 Series available from VTI Technologies Oy (http://www.vti.fi), model SQ-XL-DAQ from (http://signalquest.com). The SQ-XL-DAQ functions as a self contained data acquisition system for 2 axis or 3 axis acceleration, tilt, and vibration measurement when used with a serial interface cable.

It is envisioned that accelerometers may be used in combination with gyroscopes, where gyroscopes detect rotation and where the accelerometers detect acceleration, for sensing inertial movement within a three-dimensional space.

It is also within the scope of the present invention that sensors 10, 10' include inclinometers to measure roll angle and pitch angle in one or more of the exemplary embodiments discussed above. An exemplary inclinometer for use with the present invention is model SQ-S12X-360DA from Signal Quest, Inc. (http://www.Signalquest.com). Such an exemplary inclinometer provides both an analog voltage output and a digital serial output corresponding directly to a full-scale range of 360.degree. of pitch angle and 180.degree. of roll angle. Another exemplary inclinometer for use with the present invention is model SCA61T Series available from VTI Technologies Oy (http://www.vti.fi). The measuring direction for this exemplary inclinometer is parallel to the mounting plane.

It is also within the scope of the invention that the sensors 10, 10' include magnetometers for detecting an artificial magnetic field and/or the earth's magnetic field and discerning positional data therefrom. An exemplary magnetometer for use with the present invention is model CXM544 available from Crossbow Technology, Inc. (http://www.xbow.com). The magnetometer is capable of detecting the earth's magnetic field in three axes and computes a continuous measure of orientation using a 3-axis accelerometer as a gravitational reference field. The magnetometer compensates for temperature drift, alignment, and other errors.

Another exemplary magnetometer for use with the present invention includes model HMC1053 available from Honeywell, Inc. (http://www.magneticsensors.com). Such an exemplary magnetometer includes a wheatstone bridge to measure magnetic fields. With power supply applied to a bridge, the sensor converts any incident magnetic field in the sensitive axis direction to a differential voltage output. In addition to the bridge circuit, the sensor has two on-chip magnetically coupled straps; the offset strap and the set/reset strap. These straps are for incident field adjustment and magnetic domain alignment, and eliminate the need for external coils positioned around the sensors. The magnetoresistive sensors are made of a nickel-iron (Permalloy) thin-film deposited on a silicon wafer and patterned as a resistive strip element. In the presence of a magnetic field, a change in the bridge resistive elements causes a corresponding change in voltage across the bridge outputs. These resistive elements are aligned together to have a common sensitive axis (indicated by arrows) that will provide positive voltage change with magnetic fields increasing in the sensitive direction. Because the output only is in proportion to the one-dimensional axis (the principle of anisotropy) and its magnitude, additional sensor bridges placed at orthogonal directions permit accurate measurement of arbitrary field direction. The combination of sensor bridges in two and three orthogonal axes permits applications such as compassing and magnetometry.

Figure 22:
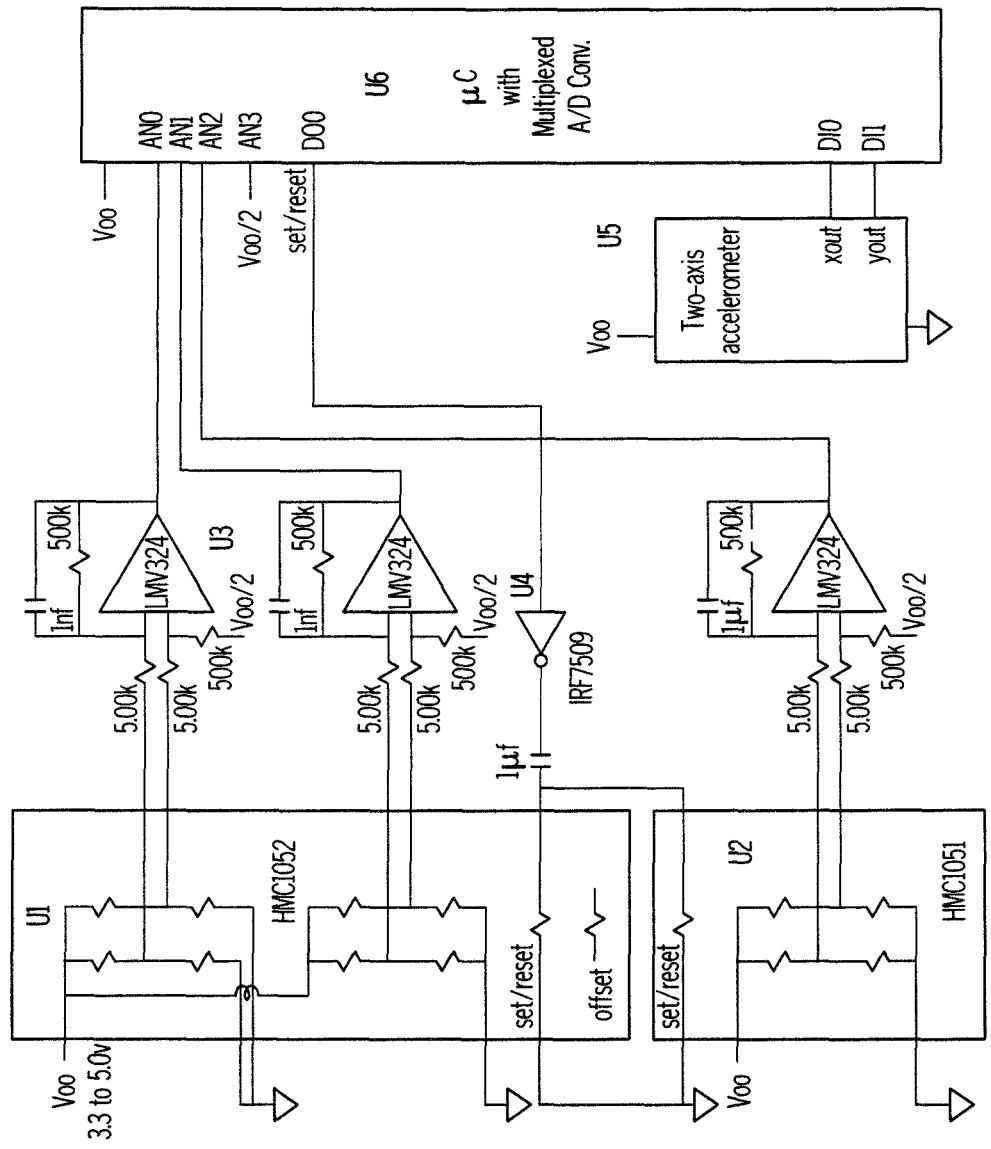
FIG. 22 is a schematic circuit diagram representation of a three-axis magnetic field detector set up.

Referring to FIG. 22, an exemplary three-axis magnetic field detector may comprise a two-axis detector combined with a single axis detector. Alternatively a single three axes detector may be used in place of the above combination.

In accordance with the present invention, the sensors may be connected to one or more displays and digital recording devices via wire and/or wireless transmission. A first exemplary embodiment includes a sensor operatively coupled to a radio frequency (RF) modem that may include a programmed microprocessor (i.e., a smart modem). The microprocessor may organize the data into discrete packets and address such packets for reception by intended remote displays and/or digital recording devices. Each of the displays and/or digital recording devices also include a smart modem operative to automatically discern if the data is corrupted and if the data is intended for that particular remote device. If the data is corrupted, the smart modem will signal the disseminating modem to resend the data. The packetizing and addressing of the packets reduces interference and enables the same radio frequency to be utilized by each of the smart modems.

Alternatively, the present invention may utilize dumb modems transmitting data on a predetermined frequency. One of ordinary skill is familiar with the software and hardware that may be associated with a dumb modem to provide addressing and data packetization.

It is also within the scope of the invention that the sensors be operatively coupled to a dumb modem and radio frequency transmitter that manipulates the data output from the sensors and converts it into a radio signal. The radio signal is adapted to be received by one or more remote devices, where a modem operatively coupled thereto converts the radio signals into data indicative of data output by the sensors regarding at least one of position, acceleration, and velocity.

An exemplary RF modem may utilize an RF spread spectrum radio transmitter or may utilize another RF communication protocol.

Following from the above description and invention summaries, it should be apparent to those of ordinary skill in the art that, while the apparatuses described herein constitutes an exemplary embodiments of the present invention, the invention contained herein is not limited to this precise embodiments and changes may be made to the aforementioned embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any one of the claims, since the invention is defined by the claims and since inherent and/or unforeseen advantages of the present invention may exist even though they may not have been explicitly discussed herein.

The invention claimed is:

1. A surgical telemetry system comprising: a sensor mounted to a surgical device, the sensor taken from the group consisting of an accelerometer, a magnetometer, a gyroscope, or an inclinometer; a digital processing device operatively coupled to the sensor to receive data derived from data output from the sensor, the digital processing device generating a display output; and a display operatively coupled to the digital processing device and adapted to receive the display output, where the display output displays the change in at least one of position and orientation of the sensor with respect to a point of reference.

2. The surgical telemetry system of claim 1, wherein the surgical device includes at least one of a cup inserter, a cup alignment instrument, a femoral component broach, a guiderod of an intramedullary femoral and tibial cutting jig, an extramedullary femoral and tibial cutting jig, a screw cap dome, a prosthetic knee tibial tray, a prosthetic knee trial stem, a prosthetic knee trial tibial tray, a prosthetic knee femoral component, a prosthetic knee trial femoral component, a prosthetic hip femoral component, and a prosthetic hip trial femoral component.

3. The surgical telemetry system of claim 2, wherein: the sensor is operatively coupled to a remote transmitter adapted to transmit signals indicative of sensor output as at least one of orientation and position of the sensor changes; and the digital processing device is operatively coupled to a receiver adapted to receive transmission signals from the remote transmitter; wherein the digital processing device generates display instructions for displaying at least one of the orientation and position of the sensor.

4. The surgical telemetry system of claim 3, wherein the processing device is programmed to output display instructions including the relative dimensions of the surgical device, where the output display correlates the position of the sensor with respect to at least one of the orientation and position of the surgical device.

5. The surgical telemetry system of claim 3, wherein the display is adapted to display the relative dimensions of the surgical device, where the display correlates the position of the sensor with respect to at least one of the orientation and position of the surgical device.

6. The surgical telemetry system of claim 1, wherein the system is adapted for use with total knee arthroplasty.

7. The surgical telemetry system of claim 1, wherein the system is adapted for use with total hip arthroplasty.

8. The surgical telemetry system of claim 1, wherein the surgical device includes at least one of a surgical saw, a surgical drill, a surgical hammer, a surgical reamer, and a surgical screwdriver.

9. The surgical telemetry system of claim 8, wherein the surgical device includes a plurality of sensors mounted thereto.

10. The surgical telemetry system of claim 9, wherein the surgical device includes a plurality of sensors mounted thereto, where the plurality of sensors are taken from the group consisting of an accelerometer, a magnetometer, a gyroscope, or an inclinometer.

11. A surgical telemetry system comprising: a computer system having signal conditioning hardware and software; a first surgical instrument having a first instrument positional sensor carried thereon, the first instrument positional sensor being operatively coupled to the signal conditioning hardware and software of the computer system to transmit first instrument positional data thereto; and a second surgical instrument having a second instrument positional sensor carried thereon, the second instrument positional sensor being operatively coupled to the signal conditioning hardware and software of the computer system to transmit second instrument positional data thereto, the instrument positional sensors taken from the group consisting of at least one of an accelerometer, a magnetometer, a gyroscope, and an inclinometer.

12. The surgical telemetry system of claim 11, wherein the computer system is configured to process the first instrument positional data and the second instrument positional data to generate relative position data indicative of the relative position of the first surgical instrument with respect to the second surgical instrument.

13. The surgical telemetry system of claim 12, wherein the computer system is further configured to generate at least one of audio and visual feedback of the relative position data.

14. The surgical telemetry system of claim 13, wherein: the first surgical instrument is taken from a group consisting of an insertion device, an extraction device, an impacting device, a positioning device, a surgical reamer, a surgical saw, a cutting jig, a surgical drill, a hole-starter, a surgical screw, a surgical bolt, a surgical screw-driver, a surgical bolt-driver and a material applicator; and the second surgical instrument is taken from a group consisting of a reference component; an insertion device, an extraction device, an impacting device, a positioning device, a surgical reamer, a surgical saw, a cutting jig, a surgical drill, a hole-starter, a surgical screw, a surgical bolt, a surgical screw-driver, a surgical bolt-driver and a material applicator.

15. The surgical telemetry system of claim 11, wherein: the first surgical instrument is taken from a group consisting of an insertion device, an extraction device, an impacting device, a positioning device, a surgical reamer, a surgical saw, a cutting jig, a surgical drill, a hole-starter, a surgical screw, a surgical bolt, a surgical screw-driver, a surgical bolt-driver and a material applicator; and the second surgical instrument is taken from a group consisting of a reference component; an insertion device, an extraction device, an impacting device, a positioning device, a surgical reamer, a surgical saw, a cutting jig, a surgical drill, a hole-starter, a surgical screw, a surgical bolt, a surgical screw-driver, a surgical bolt-driver and a material applicator.

16. A surgical telemetry system comprising: a computer system having signal conditioning hardware and software; a field generating device including at least one magnet generating a detectable field approximate a reference object; and at least one of a surgical instrument and a prosthetic component having a magnetometer carried thereon for sensing the detectable field, the magnetometer being operatively coupled to the signal conditioning hardware and software of the computer system to transmit positional data thereto relative to the detectable field.

17. The surgical telemetry system of claim 16, wherein the field generating device has a plurality of magnets adapted to be positioned about a circumference of a patient's acetabulum.

18. The surgical telemetry system of claim 16, wherein the field generating device is adapted to be mounted within a patient's anatomy.

19. The surgical telemetry system of claim 16, wherein the computer system is further configured to generate at least one of audio and visual feedback of the positional data.

* * * * *